(12) United States Patent
Schabron et al.

(10) Patent No.: US 6,773,921 B1
(45) Date of Patent: Aug. 10, 2004

(54) PREDICTING PROXIMITY TO COKE FORMATION

(75) Inventors: John F. Schabron, Laramie, WY (US); Joseph F. Rovani, Jr., Laramie, WY (US)

(73) Assignee: The University of Wyoming Research Corporation, Laramie, WY (US)

( * ) Notice: Subject to any disclaimer, the term of this patent is extended or adjusted under 35 U.S.C. 154(b) by 352 days.

(21) Appl. No.: 10/009,863

(22) PCT Filed: Jun. 9, 2000

(86) PCT No.: PCT/US00/15950
§ 371 (c)(1),
(2), (4) Date: Dec. 10, 2001

(87) PCT Pub. No.: WO00/77120
PCT Pub. Date: Dec. 21, 2000

Related U.S. Application Data
(60) Provisional application No. 60/138,846, filed on Jun. 10, 1999.

(51) Int. Cl.[7] .............................................. G01N 33/24

(52) U.S. Cl. ............................ 436/29; 436/31; 436/25; 436/140; 436/163

(58) Field of Search ............................. 436/29, 31, 25, 436/140, 163

(56) References Cited

PUBLICATIONS

Laux et al. "Boundaries of colloid stability of crude oils" Erdoel, Erdgas, Kohle (1998), 114(1), 25–29.*
Schabron et al. "The solubility and three–dimensional structure of asphaltenes", Petroleum Science and Technology (1998), 16(3 & 4), 361–375.*
Castillo et al. "New techniques and methods for the study of aggregation, adsorption, and solubility of asphaltenes. Impact of these properties on colloidal structure and flocculation", Petroleum Science and Technology (2001), 19(1 & 2), 75–106.*
Pillon "Effect of experimental conditions and solvents on the precipitation and composition of asphaltenes" Petroleum Science and Technology (2001), 19(5 & 6), 673–683.*
Acevedo et al. "A unified view of the colloidal nature of asphaltenes" (1995), 131–54. Editor(s): Sheu, Eric Y.; Mullins, Oliver C.*
Wiehe "Two–dimensional solubility parameter mapping of heavy oils" Fuel Science & Technology International (1996), 14 (1 & 2), 289–312.*
Yarranton et al. "Molar mass distribution and solubility modeling of asphaltenes", AIChE Journal (1996), 42(12), 3533–3543.*
"Effects of asphaltene aggregation in model heptane–toluene mixtures on stability of water–in–oil emulsions" Journal of Colloid and Interface Science (1997), 196(1), 23–24.*

(List continued on next page.)

*Primary Examiner*—Yelena G. Gakh
(74) *Attorney, Agent, or Firm*—Santangelo Law Offices P.C.

(57) ABSTRACT

Indicia of stability or thresholds of instability may be used to assess the proximity of hydrocarbon materials such as petroleum residua to deposition of carbon rich materials. The invention may be used to evaluate suitability of such hydrocarbon materials to various types of processing methodologies, or to determine processing parameters, either prior to processing or during processing. Prediction of proximity to deposition of carbon rich materials may result in continuous process parameters or increased output, decreased energy use or decreased amount of emissions per unit of such hydrocarbon materials compared to conventional processing technology. Products produced or products processed with this technology may also have a higher level of purity.

32 Claims, 13 Drawing Sheets

OTHER PUBLICATIONS

Andersen, S.I. and K.S. Birdi, 1991, "Aggregation of Asphaltenes as Determined by Calorimetry," *Journal of Colloid and Interface Science*, 142, 497–502, 1991.

Barton, A.F. 1974, "Solubility Parameters." *Chemical Reviews*, 75 (6), 731–753.

Burrell, H., 1955, "Solubility Parameters." *Interchemical Review*, 3–16.

Heithaus, J. J. 1962, "Measurement and Significance of Asphaltene Peptization." Journal of the Institute of Petroleum 48 (458). 45–53.

Hildebrand, J.H., J.M. prausnitz. and R.L. Scott, 1970, "Regular and Related Solutions," Van Nostrand Reinhold, NY. pp. 24–27, pp 152–153, pp 212–215.

Long, R.B. and J.G. Speight, 1989, "Studies in Petroleum Composition." *Revue de l'Institute Francais du Petrole*, 44 (2), 205–217.

Long, R.B., 1979, "The Concept of Asphaltenes," *Preprints. Div. Petroleum Chemistry, American Chemical Society*, 24, 891–901.

Pauli, A.T. 1996, "Asphalt Compatibility Testing Using the Automated Heithaus Titration Test." *Preprints. Division of Fuel Chemistry, American Chemical Society*, 41(4), 1276–1281.

Scatchard, G. 1931. "Equilibria in Non–Electrolyte Solutions in Relation to the Vapor Pressure and Densities of the Components," *Chemical Reviews*, 321–333.

Schabron, J.F. and J.G. Speight 1998, "The Solubility and Three–Dimensional Structure of Asphaltenes," *Petroleum Science and Technology*, 16 (3–4), 361–376.

Schabron, J.F., G.W. Gardner, J.K. Hart, N.D. Niss, G. Miyake, and D.A. Netzel. 1993, "The Characterization of Petroleum Residua" U.S. Dept of Energy Report DE/MC/11076–3539 Small, P.A., 1953, "Some Factors Affecting the Solubility of Polymers," Journal of Applied Chemistry, 71–80.

Snyder, L.R., 1968, Principles of Adsorption Chromatography, Marcel Dekker, Inc., New York, 206–210.

Wiehe, I.A., 1996, "Two–Dimensional Solubility Parameter Mapping of Heavy Oils, " *Fuel Science and Technology International*, 14 (1&2), 289–312.

"Standard Test Method for Molecular Weight (Relative Molecular Mass) of Hydrocarbons by Thermoelectric Measurement of Vapor Pressure," ASTM Designation: D 2503–82 (Reapproved 1987), 211–213.

US Provisional Application, entitled "Predicting Proximity to Coke Formation", filed Jun. 10, 1999, 24 pages and 7 drawings.

* cited by examiner

PREDICTING PROXIMITY TO COKE FORMATION

This application is the United States National Stage of International Application No. PCT/US00/15950, filed Jun. 9, 2000 which claims the benefit of U.S. Provisional Application No. 60/138,846, filed Jun. 10, 1999, each hereby incorporated by reference.

TECHNICAL FIELD

Generally, methods and apparatus for evaluating or processing hydrocarbon materials having unimodal characteristics which may acquire multimodal characteristics upon processing. Specifically, indica of stability for hydrocarbons having unimodal characteristics which may be used separately, or used in combination, or used in comparison to a determined threshold of instability for such unimodal characteristics, to assist in determining the proximity of hydrocarbon materials having unimodal characteristics to formation of multimodal characteristics, or to assist in pre-determining the degree of acquired multimodal characteristics in response to various processing parameters.

BACKGROUND

It can be difficult to evaluate, in response to a given set of processing parameters, if, or when, or to what degree, a hydrocarbon material of homogeneous mixture may transition to a hydrocarbon material of heterogeneous mixture to form carbon rich materials, such as coke. When hydrocarbon materials, such as heavy oils, petroleum residua, shale oils, coal tars, tar sand bitumen, asphalts, or the like, are processed at non-pyrolytic temperatures (at or below 340° C. or 644° F.), or are heated above the temperature at which pyrolysis occurs (at about 340° C. or 644° F.), there is typically an induction period before deposition of carbon rich materials occurs. This induction period can be variable, ranging from a few seconds to hours, depending on the particular hydrocarbon material and the temperature at which it is processed. To avoid deposition of carbon rich material refiners often process hydrocarbon materials based on arbitrary criteria Because arbitrary criteria are used, conventional processing of hydrocarbon materials can result in product yields that may not be maximal.

Because of the substantial benefits that can result from predicting if, when, or to what degree particular processing parameters may induce hydrocarbon materials to form heterogeneous mixtures; there has been extensive commercial interest in technology to define indicia of stability with respect to the homogeneous mixture, or to define thresholds of instability at which transition to the heterogeneous mixture may occur. Such indica of stability or thresholds of instability for hydrocarbon materials may be used, for example, to evaluate the suitability of hydrocarbon materials for particular types of processing, to predict the proximity to carbon deposition or coke formation, or for controlling hydrocarbon material processing in a manner which eliminates, minimizes, or predicts the amount of carbon deposition or coke formation. Even though commercial interest has generated substantial research in various fields, a long felt but unresolved need remains for methods of determining when hydrocarbon materials comprise homogeneous mixtures, or for development of indicia of stability for such homogeneous mixtures, or for more objective thresholds of instability for such homogeneous mixtures to assist in predicting proximity to formation of heterogeneous mixtures. See for example, U.S. Pat. No. 5,853,565, hereby incorporated by reference. As such, substantial problems with respect to the evaluation of hydrocarbon materials for processing, or to the processing of hydrocarbon materials, remained unresolved.

A significant problem with conventional technology for the evaluation and processing of hydrocarbon material may be the failure of conventional technology to define, provide measures for, or interpretations of, the dynamics of unimodal characteristics of intact hydrocarbon materials. Unimodal characteristics define a comprehensible pattern of attributes having predictable variation to changing environmental or processing parameters. As such, unimodal characteristics make possible the development of ascertainable indicia for comparative evaluation of the functionally related components that make up a hydrocarbon material. Ascertainable indicia can make the response of hydrocarbon materials to such environmental or processing parameters predictable. Unimodal characteristics may also provide objective indica for the manufacture of hydrocarbon material products to assure that components have an anticipated degree of association. As can be understood, conventional technology has focused upon evaluation of the characteristics of separated components of hydrocarbon materials. The data obtained by evaluation of these isolated components is then typically used to determine the differences between types of hydrocarbon materials. However, conventional evaluation of isolated components does not provide a substantial amount of information about the intact hydrocarbon material itself. It can be understood that while conventional technology may understand that a hydrocarbon materials can be made up of chemical components, or that conventional technology may understand that the chemical components have a certain physical relationship or distribution with respect to one another, conventional technology may provide, if at all, only a limited insight about the dynamic behavior of the various components of a hydrocarbon materials to changing environmental or processing parameters, or how the components functionally relate to maintain the stability of their physical association. As such, conventional technology may not provide suitable indica of stability, thresholds of instability, or the methods for comparing such indicia of stability to such thresholds of instability which are the ascertainable measures of the unimodal characteristics of intact, unseparated hydrocarbon material. Indeed, conventional technology affords few, if any, tools for diagnosing or predicting how a hydrocarbon material will behave under a specific set of circumstances.

Another significant problem with conventional technology for the evaluation and processing of hydrocarbon material may be formation of carbon rich material during non-pyrolytic events (at or below about 340° C.). The deposition of carbon rich material, such as coke, can result in fouling of heat exchange devices, or other refinery equipment in both upstream and downstream operations. This equipment may have to be shut down for mechanical coke removal as disclosed by Schabron, J. F. et al., *Deposition From Heavy Oils*, pp. viii and 2, (2000), hereby incorporated by reference.

Another significant problem with conventional technology for the evaluation and processing of hydrocarbon material may also be the formation of carbon rich deposits, such as coke, from pyrolytic events (at or above about 340° C.). Deposition of carbon rich material, such as coke, from pyrolytic events during processing can also result in the problems described above including having to shut down processing equipment for mechanical removal of the deposited materials.

Another significant problem with conventional technology for the evaluation and processing of hydrocarbon material may be the lack of a method or use of arbitrary criteria for predicting the proximity of a hydrocarbon material to the point of transition from a homogenous mixture of components to a heterogeneous mixture of components, including the proximity to carbon deposition or coke formation.

Another significant problem with conventional technology for the evaluation and processing of hydrocarbon material may be a low yield of liquid distillates. The use of arbitrary criteria to assess the stability of a homogeneous mixture of hydrocarbon materials, or to predict when carbon deposition may occur, can result in distillation parameters for the hydrocarbon material that stop the distillation sooner than need be to avoid deposition of carbon rich materials, such as coke. When distillation is stopped sooner than is necessary to avoid carbon deposition, it can result in less than maximal product yield from the hydrocarbon material. In 1997, for example, the average United States atmospheric and vacuum distillation refinery capacity was about 23 million barrels per day as disclosed by the Department of Energy, *OIT Report*, p. 5, (1998), hereby incorporated by reference. Solvent deasphalting capacity was about 0.3 million barrels per day. About 1.8 million barrels per day of heavy end feedstocks produced in 1997 from atmospheric and vacuum distillation columns and solvent-deasphalting units were input to thermal cracking and coking operations. This represents about 10% of the crude run. Id. at p. 49. An additional 6.5 million barrels per day went into catalytic cracking and hydrotreating units. Based on the total of 1.8 million barrels of total heavy ends minus about 0.3 million from solvent deasphalting, about 1.5 million barrels of heavy ends per day of thermal cracking and coking feed are produced from distillation operations. Assuming a one percent increase in United States distillate output because of efficiency improvements, an increase of about 15,000 average barrels per day of distillate and a corresponding reduction of heavy ends would result. Efficiency increases well above 1% could be possible if the proximity to carbon deposition or coking for a hydrocarbon material could be measured.

Another significant problem with conventional technology for the evaluation and processing of hydrocarbon material may be the inefficient use of energy. Coking operations use about 166,000–258,000 Btu per barrel of hydrocarbon material fees Department of Energy, *OIT Report*, pp. 62–63, (1998). Hydrotreater energy use is comparable, and a similar consideration may apply. Since most of the energy used can be to initially heat all of the hydrocarbon feed material for distillation, there may be only minimal extra heat required to obtain a 1% improvement of distillate output at a particular temperature. For each 1% decrease in hydrocarbon material feed, there would be a potential savings of about 2.5–3.9 billion Btu with respect to hydrocarbon materials that do not need to be heated for coking, since they will have been recovered in an optimized distillate stream.

Another significant problem with conventional technology for the evaluation and processing of hydrocarbon material may be high emissions. An energy savings of about 2.5–3.9 billion Btu per day, as discussed above, can result in a corresponding lowering of emissions from fuel that is not burned in processing operations. For example, residual fuel used as the heat source produces about 174 pounds of carbon dioxide per million Btu generated Department of Energy, *OIT* Report, pp. 27, (1998). Thus, in the U.S., the reduction in carbon dioxide emissions for each 1% industry-wide efficiency improvement may be about 218–679 tons per day!

Another significant problem with conventional technology for the evaluation and processing of hydrocarbon material may be financial losses. The disruption of hydrocarbon material processing from fouling due to deposition of carbon rich material, such as coke, is pervasive throughout the industry. The financial losses due to unscheduled downtime events as a result of non-pyrolytic, or of pyrolytic, deposition of carbon rich materials such as coke, may be difficult to quantify, but they are important.

Another significant problem with conventional technology for the evaluation and processing of hydrocarbon material may be that the liquid products of distillation may be of lower quality. Interrupting the distillation process, or proceeding with the distillation process in steps or stages, to avoid deposition of carbon rich materials or coke may allow for contamination of the liquid distillates.

Yet another significant problem with existing methods of processing hydrocarbon materials may be lack of a method for predicting the amount of initial deposition of carbon rich material or coke formation upon pyrolysis of a hydrocarbon material.

Still another significant problem with existing methods of processing of hydrocarbon materials may be the lack of apparatus or methods that are practical, convenient, or provide for real time data with respect to the stability of hydrocarbon materials.

With respect to processing hydrocarbon materials in general and specifically with respect to characterizing the dynamics of unseparated, intact hydrocarbon materials including predicting proximity to carbon deposition or coke formation, it can be understood there exists an array of problems which have remained unresolved by use of conventional hydrocarbon processing technology. The present invention addresses each of the above-mentioned problems and provides practical solutions.

DISCLOSURE OF THE INVENTION

Indica which define unimodal characteristics of hydrocarbon materials, or indicia which estimate the stability of such unimodal characteristics of hydrocarbon materials which may be used separately or may be used in combination, or may be u in comparison to determined threshold of instability for such unimodal characteristics, to assist in determining the proximity of such unimodal characteristics to formation of multimodal characteristics, or to assist in predicting the degree of acquired multimodal characteristics in response to various processing parameters.
Naturally, as a result of these several different and potentially independent aspects of the invention, the objects of the invention are quite varied.

A broad object of a particular embodiment of the invention can be to establish values for various associations between components of a hydrocarbon material which define the attributes or characteristics of a unimodal system. One aspect of this object can be to provide a value for the size of a core material in comparison to the size of the core material having sufficient solvent salvation shell to maintain unimodal character ($K_s$) A second aspect of this object can be to provide an average value for the relative size ratio of a plurality of solvated core materials and the size of the plurality of solvated core materials having sufficient associated solvent (for example trapped solvent between them) to maintain unimodal character ($K_F$). A third aspect of this object can be to provide a value for the solvation shell and associated solvent about a core particle or plurality of core particles to maintain unimodal characteristics (K) where $K = K_S \cdot K_F$.

A second broad object of a particular embodiment of the invention can be to provide indicia of stability for the above-mentioned unimodal characteristics exhibited by hydrocarbon materials. Indicia of stability are values that result from measuring the degree of association between certain components in the hydrocarbon material which can allow assessment of the stability of a unimodal characteristic at a given point in time. Having objective values that reflect the instant degree of stability of the unimodal characteristics can be useful in evaluating suitability of hydrocarbon materials for various types of processing parameters, or for maintenance of unimodal characteristics during hydrocarbon processing.

Another broad object of a particular embodiment of the invention can be to establish thresholds of instability. A threshold of instability establishes a degree of association (or lack of association) between components of a hydrocarbon material at which acquisition of multimodal characteristics by the hydrocarbon material may be expected. These thresholds of instability may be used in conjunction with the above-mentioned indica of stability to assess the proximity of hydrocarbon materials having unimodal characteristics to the threshold of instability or to acquisition of multimodal characteristics.

Another object of a particular embodiment of the invention can be to provide indicia of stability or to establish thresholds of instability based upon instrumented measurement of various size ratios which correlate with unimodal characteristics. The size ratio of the core material to the core material with associated solvent ($K_S$), or the ratio of an average size of a plurality of solvated core materials with an associated solvent to an average size of a plurality of solvated core materials, thus representing an amount of associated solvent associated with a plurality of solvated core materials ($K_F$), or the solvation shell about a core particle or plurality of core particles (K) where $K=K_s \cdot K_F$, independently or in combination can be useful in measuring unimodal character of a hydrocarbon material. These size relationships may be evaluated by the use of various instrumented techniques such as nuclear magnetic resonance spectroscopy, nuclear magnetic resonance tomography, mass spectrometry, infrared spectrometry, raman spectroscopy, size exclusion chromatography, gel electrophoresis device, and paper chromatography.

Another object of a particular embodiment of the invention can be to provide indicia of stability related to the molecular weight of particular components in a hydrocarbon material which correlate with the stability of unimodal characteristics.

Another object of a particular embodiment of the invention can be to provide indicia of stability based upon the distribution of various polar components in hydrocarbon materials. One aspect of this embodiment of the invention may be an indicia of stability determined as the amount of asphaltenes soluble in particular solvent having a particular polarity. Of course, the tern "amount" generally, may include any of different kinds of measurements such as, but not limited to, quantities, lengths, sizes, volumes, weights, weight percentages, weight fractions, volume percentages, volume fractions, radii, diameters, circumferences, or the like, however measured such as but certainly not limited to ultrasound spectroscopy, microscopy, filtration, solvation, titration, NMR spectroscopy, NMR tomography, mass spectrometry, infrared spectrometry, infrared Raman spectroscopy, size exclusion chromatography, gel electrophoresis, paper chromatography, or the like. For example, the amount of asphaltenes precipitated with heptane soluble in cyclohexane can be diagnostic of the stability of the unimodal character of hydrocarbon materials. A second aspect of this embodiment of the invention can be an indicia of stability determined as the ratio of the weight percent of solvent soluble asphaltenes to the weight percent asphaltenes that are not solvent soluble. For example, the ratio of the weight percent of the cyclohexane soluble portion of the heptane precipitated asphaltenes to the weight per cent of the heptane precipitated asphaltenes appears to provide a sensitive indicator of stability of the unimodal character of hydrocarbon materials. A third aspect of this embodiment of the invention can be an indicia of stability based upon titration data. This involves the a titration of solutions of hydrocarbon material with a weak solvent to the point of asphaltene precipitation. An indicia of stability can be described based on the titration data defined as $p_a/C_{min}$.

Another object of a particular embodiment of the invention can be to use the determined indicia of stability in comparison to the established thresholds of instability to assess the proximity of unimodal characteristics to the threshold of instability. One aspect of this object of the invention can be to predict the proximity of a hydrocarbon material to coke formation.

Another object of a particular embodiment of the invention can be to use the indicia of stability, individually or in combination to evaluate hydrocarbon materials prior to processing or during processing to model substantially continuous distillation parameters for a particular hydrocarbon material or mixture hydrocarbon materials.

Another object of a particular embodiment of the invention can be optimization of the yields of distillable liquids from a hydrocarbon material having unimodal characteristics. Any increase in the yield of distillable liquids from the same amount of hydrocarbon material such as heavy oil or petroleum residuum provides an immediate increase in revenue. As such, a method of optimizing yields of distillable liquids has immediate and important commercial applications.

Another object of a particular embodiment of the invention can be to predict the degree of multimodal characteristics that may be acquired by a particular hydrocarbon material with respect to various processing parameters. One aspect of this object may be to predict the initial amount of carbon rich material, such as coke, that may be formed upon processing of a hydrocarbon material with particular processing parameters.

Another object of a particular embodiment of the invention can be to save energy. There may be a significant energy savings involved when a higher yield of distillates is produced from the same amount of hydrocarbon material. As described above, there may be only a minimal amount of extra heat required for a 1% improvement of distillate output at a particular temperature since the majority of the energy is used to initially heat all the hydrocarbon material for distillation. For each 1% decrease in the amount of distillate bottoms heated for a subsequent coking operation in the United States a potential savings in energy of about 2.5 billion Btu to about 3.9 billion Btu per day may be realized.

Another object of a particular embodiment of the invention can be to reduce emissions. The above-mentioned potential savings in energy of about 2.5 billion Btu to about 3.9 billion Btu results in a corresponding reduction in emissions from fuel that is not burned in processing additional hydrocarbon material. For example, residual fuel used to as the heat source for processing produces about 174 pounds of carbon dioxide per million Btu generated. Department of Energy, *QIT Report*, p. 27 (1998), hereby incorporated by reference. Thus in the United States, the reduction in carbon dioxide emission for each 1% industry-wide efficiency improvement is about 218–679 tons.

Another object of a particular embodiment of the invention can be to produce higher initial quality as compared to conventional liquid distillables. Because the process of distillation may be nearly continuous, the distillates may have fewer opportunities to collect water and become otherwise contaminated. This may result in higher purity distillates and perhaps lower post distillation processing costs. As such, distillates from near continuous distillation processes made possible from the instant invention may be distinguishable from conventional distillation products.

Still another object of a particular embodiment of the invention can be to provide a molecular weight/polarity map system to assess the solubility of various components in a mixture of asphaltene complexes at various distillation parameters. Such a map system may provide an evaluation method for diagnosing processing conditions for hydrocarbon materials having unimodal characteristics prior to or during distillation.

Yet another object of a particular embodiment of the invention can be to establish a sequential solvent extraction system to isolate various asphaltene complexes from hydrocarbon materials having unimodal characteristics based on molecular weight or polarity.

Naturally further objects of the invention may be disclosed throughout other areas of the specification and claims.

MODE(S) FOR CARRYING OUT THE INVENTION

Figure 1:
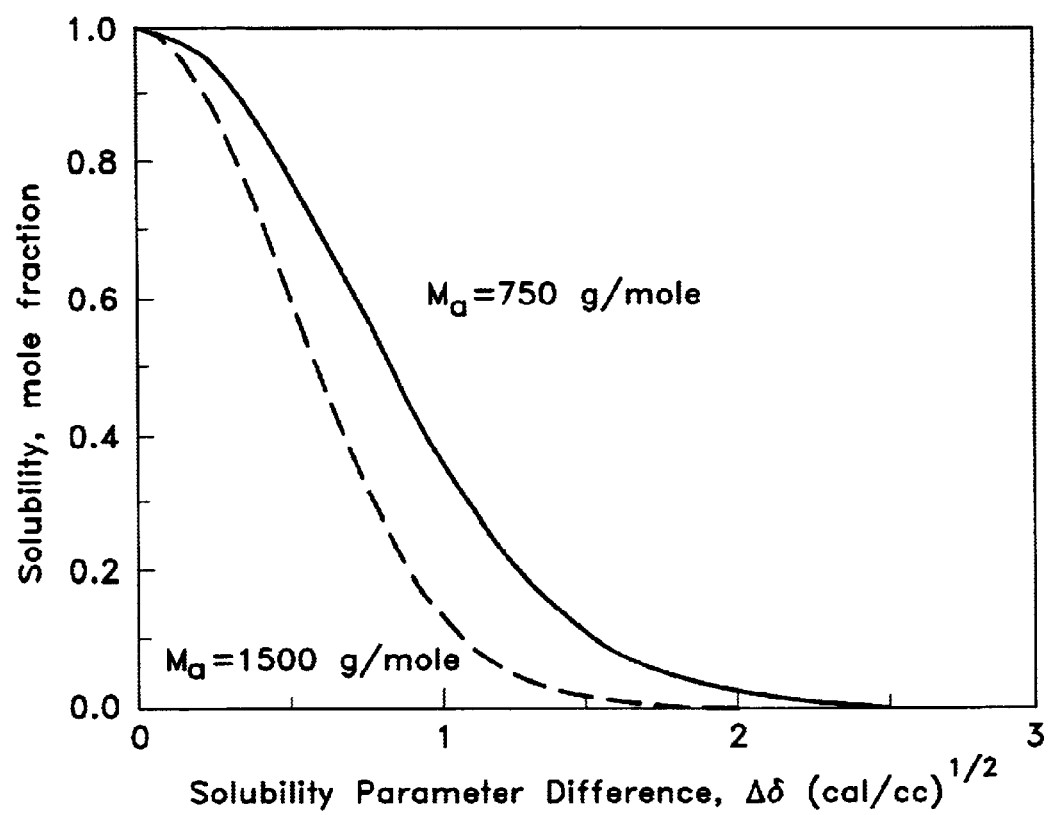
FIG. 1 shows the relationship between solubility and solubility parameter difference.

Hydrocarbon materials, such as heavy oils, petroleum residua, coal tars, shale oils, asphalts, or the like can comprise polar core materials, such as asphaltenes, dispersed in lower polarity solvent(s). Intermediate polarity material(s), usually referred to as resin(s), can associate with the polar core materials to maintain a homogeneous mixture of the components. The invention focuses on novel unimodal characteristics which are ascertainable aspects of the relationship, or degree of association, between these components that can maintain the hydrocarbon material as a homogeneous mixture. Alternately, the lack of, or diminishment of these ascertainable aspects of the unimodal character can used to predict the onset or degree of acquired (and perhaps undesirable) multimodal characteristics associated with formation of the resulting heterogeneous mixture.

As one example, refinery processes, including but not limited to, atmospheric or vacuum distillation, visbreaking, hydrocracking, delayed coking, Fluid Coking, FLEXICOKING, or Eureka that convert hydrocarbon materials to lighter distillate fuels require heating for distillation, hydrogen addition, or carbon rejection (coking). However, when using conventional refinery processes, the efficiency of converting such hydrocarbon material may be limited by transition of the hydrocarbon material of homogeneous mixture to a hydrocarbon material of heterogeneous mixture. The transition to the heterogeneous mixture may include the formation of insoluble carbon-rich coke deposits, including the formation of coke. As such, any reduction in carbon deposition, or increase in the distillation yield during the thermal processing of hydrocarbon material can have a significant impact on the manner or economics of hydrocarbon processing.

The invention, in contrast to conventional processing technology, provides ascertainable unimodal characteristics as the basis for measures of stability with respect to hydrocarbon materials that transit between homogenous mixtures and heterogenous mixtures of components, methods for assessing the degree of the such unimodal characteristics, methods for predicting the proximity of hydrocarbon materials having unimodal characteristics from the threshold of acquiring multimodal characteristics, or methods for predicting the degree of multimodal characteristics acquired due to various processing parameters.

Specifically, the invention provides indicia of stability, thresholds of instability, methods for comparing such indicia of stability with such thresholds of instability so that hydrocarbon materials can be evaluated for processing, for selecting processing parameters to avoid carbon deposition, or for reaching predetermined levels of carbon deposition, for increasing the yield of liquid distillates, for decreasing emissions from processing, or for reducing the consumption of energy. In this application, each are disclosed as part of the results shown to be achieved by the various methods and devices described and as steps which are inherent to utilization. In addition, while a variety of methods are disclosed, it should be understood that these are accomplished using certain devices but also that the methods and devices can varied in a number of ways. Importantly, as to all of the foregoing, all of these facets should be understood to be encompassed by this disclosure.

The dissolution of a material in a solvent, or the mixing of two liquids to form a homogeneous mixture, will occur if the free energy of the process is zero or negative as described by:

$$\Delta G = \Delta H - T\Delta S$$

where $\Delta G$ is the fee energy, $\Delta H$ is the heat of mixing, T is the temperature, and $\Delta S$ is the change in entropy. Typically in a dissolution process, the entropy term is relatively large, and the heat of mixing determines if the mixing will occur.

The heat of mixing may be described as:

$$\Delta H = V((\Delta E_1/V_1)^{1/2} - (\Delta E_2/V_2)^{1/2})^2 \Phi_1 \Phi_2$$

where $\Delta H$ is the heat of mixing, V is total volume, $\Delta E_x$ is the molar energy of vaporization of component x, $V_x$ is the molar volume of component x, and $\Phi_x$ is the volume fraction of component x in the solution. The term $(\Delta E/V)^{1/2}$ is called the solubility parameter $\delta$ and is typically given in units of $(cal/cc)^{1/2}$, called the Hildebrand. Numerical values for the solubility parameter of a solvent can be calculated as:

$$\delta = (\Delta E/V)^{1/2}$$

from the molar energy of vaporization to the ideal gas state, $\Delta E$ and the molar volume V. For large molecules or polymeric systems, group contributions can be used to calculate if the density of the material is known or can be estimated.

The heat of mixing two materials is dependent on the difference between their solubility parameters squared, $(\delta_1 - \delta_2)^2$. If the solubility parameters are identical, the heat of mixing is zero and the dissolution/mixing process is driven by the entropy term T$\Delta$S alone, and mixing will occur. If the solubility parameters are not identical, the term $(\delta_1 - \delta_2)^2$ will have a net positive value, which will cause the energy term $\Delta H$ to oppose the entropy term. If the entropy term is less than the energy term, mixing or dissolution will not occur.

However, the use of the solubility parameter is complicated by the presence of dipole and hydrogen bonding interactions. For solvents or materials with strong polarity or hydrogen bonding components, dissolution may not be predictable by the single component, or dispersion solubility parameter, described above. For such systems, solubility is maximized when all the components for the solvent and material being dissolved are similar in polarity. Two- or three-dimensional maps can be used to describe so-called solubility zones, areas, or spheres for such systems. Mixtures of solvents with different solubility parameter components can be used to generate a mixture with custom-formulated solubility parameter components. Thus, it is possible to formulate a mixture of two or more solvents that will dissolve a material that is not soluble in one or more of the solvents alone. For hydrocarbon materials such as petroleum residua or fractions isolated therefrom, solubility characteristics can best be described by the single-component dispersion solubility parameter. Multi-component solubility parameters are not necessary.

Selected solvents that do not have significant polarity or hydrogen bonding components are listed in Table 1, along with their solubility parameters. The solubility parameter of a mixture of solvents is the sum of the solubility parameter of each component times the volume fraction of that component in the mixture.

TABLE 1

Solubility Parameters of Solvents with Predominantly Dispersive Components

| Solvent | Solubility Parameter, $(cal/cc)^{1/2}$ |
|---|---|
| perfluoro-n-hexane | 5.9 |
| iso-octane | 6.9 |
| n-pentane | 7.0 |
| n-hexane | 7.3 |
| n-heptane | 7.4 |
| cyclohexane | 8.2 |

TABLE 1-continued

Solubility Parameters of Solvents with Predominantly Dispersive Components

| Solvent | Solubility Parameter, $(cal/cc)^{1/2}$ |
|---|---|
| toluene | 8.9 |
| benzene | 9.2 |
| carbon disulfide | 10.0 |
| diiodomethane | 11.8 |

Toluene, for example, is known to be a good solvent for hydrocarbon material such as whole petroleum residua. This is probably because the solubility parameters of whole petroleum residua components lie within about $\pm 2$ $(cal/cc)^{1/2}$ of 8.9, or within 6.9–10.9 $(cal/cc)^{1/2}$. Once thermal treatment of petroleum residua has begun, however, toluene fails to solvate the more polar components, which are formed as carbon deposition or coking ensues.

Relatively large solubility parameters require the use of polar interactive or hydrogen bonding solvents such as the alcohols (methanol $\delta$=14.6, ethanol $\delta$=12.5, etc.). Solubility parameters below those of the perfluorinated hydrocarbons can be attained by using silicone oils or supercritical fluids such as supercritical carbon dioxide.

Hydrocarbon materials, such as petroleum residua, are usually complex mixtures that are usually separated into well-defined fractions prior to characterization. Separation schemes typically include steps such as precipitation of asphaltenes by a hydrocarbon solvent such as n-heptane and subsequent separation of the deasphaltened material (maltenes) by adsorption, ion exchange, size exclusion chromatography, or combinations thereof as disclosed by Schabron, J. F., G. W. Gardner, J. K. Hart, N. D. Niss, G. Miyake, and D. A. NetzeL *The Characterization of Petroleum Residua*, United States Department of Energy Report DE/MC/11076-3539 (1993), hereby incorporated by reference. The isolation of components from hydrocarbon materials, such as asphaltenes, can be based upon a solvent separation procedure based on the solubility difference between the precipitating solvent and the precipitated material. The solubility (or lack thereof) of components of hydrocarbon materials can be dependent on both molecular weight and polarity considerations. The solubility parameter of a particular hydrocarbon material or residuum fraction probably constitutes a range that is reflective of the variety of chemical components of the fraction. The solubility parameter difference that results in a phase separation of two materials, such as asphaltenes in a solvent can be estimated using the Scatchard-Hildebrand equation, which involves several assumptions that take into account both the heat of mixing and entropy terms:

$$\ln a_a = \ln x_a + M_a/RT\rho_a \cdot [N_s^2(\delta_s - \delta_a)^2]$$

where $a_a$ is the activity of the solute a, $x_a$ is the mole fraction solubility of a, $M_a$ is the molecular weight of a, $\rho_a$ is the density of a, $N_s$ is the volume fraction of solvent, and $(\delta_s - \delta_a)$ is the difference between the solubility parameters of the solute a and the solvent s. Assuming that the activity of asphaltenes $a_a$ is 1 (solid asphaltenes in equilibrium with dissolved asphaltenes as an example) and the volume fraction of an excess of solvent is essentially 1, the equation can be rearranged into a form that can be used to gain insight into the solubility of asphaltenes:

$$\ln x_a = -M_a/RT\rho_a \cdot [(\delta_s - \delta_a)^2]$$

Assuming molecular weights of 750 and 1,500 g/mole for two hypothetical asphaltene molecules, the solubility as a function of the differences between solubility parameters of the asphaltene molecules and a range of solvent solubility parameters can be calculated.

Referring now to FIG. 1, it can be understood that the solubility of an individual asphaltene molecule or complex decreases as the difference between solubility parameters increases. Also, a lower molecular weight molecule is more soluble than the higher molecular weight molecule for a particular difference in solubility parameter. From the above equations, it is apparent that the solubility depends both on molecular weight and polarity of the particular asphaltene molecule or associated specie. In an asphaltene mixture, for example, there exists a polarity and molecular weight continuum as described by Schabron, J. F. and J. G. Speight, *The Solubility and Three-Dimensional Structure of Asphaltenes*, Petroleum Science and Technology, 16 (3–4), pp. 361–376 (1998), hereby incorporated by reference.

Figure 2:
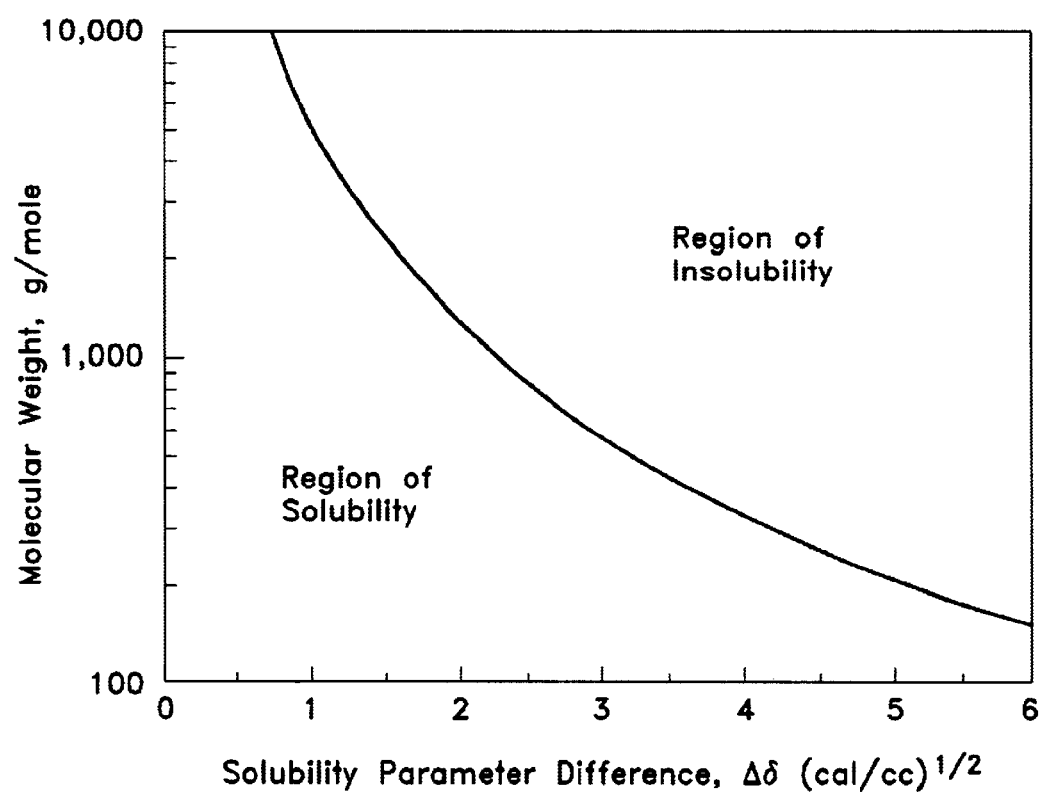
FIG. 2 shows the effects of molecular weight and solubility parameter difference on solubility.

Now referring to FIG. 2, additional information can be gleaned by calculating the solubility parameter difference at several molecular weights ranging from 100–10,000 g/mole at which the solubility of asphaltenic or other material is a mole fraction of about 0.001 (0.1%, or 1,000 ppm). The results of this calculation defines a phase diagram that is a function of molecular weight and solubility parameter difference. As can be understood from the figure both polarity and molecular weight of asphaltenes in a solvent define the solubility boundary. This conceptually describes how asphaltenes can be precipitated from hydrocarbon materials, which can be considered a type of homogeneous mixture having a continuum of molecular weights and polarities which exhibit or have certain unimodal characteristics. FIG. 2 also shows in a generalized manner that as the molecular weight of a particular solute decreases, there is an increased tolerance to polarity difference between solute and solvent under miscible conditions.

The absolute difference in solubility parameters that will result in transition from the homogeneous mixture exhibiting unimodal characteristics to the heterogeneous mixture exhibiting or having multimodal characteristics such as a two-phase system (or other poly-phase system), or precipitation of a component, or deposition of carbon, for a particular system is not straightforward. Based on the above discussions and the results illustrated in FIG. 2, some generalizations can be made. For a polymer to dissolve in a solvent, the solubility parameter of the solvent should be within about 1 $(cal/cc)^{1/2}$ of the solubility parameter of the polymer. For a non-polymeric solid material, such as naphthalene, to dissolve in a solvent, the difference in solubility parameters should be less than about 2 $(cal/cc)^{1/2}$. And finally, for two liquids to be miscible, the difference in their solubility parameters should be less than about 7 $(cal/cc)^{1/2}$.

Figure 3:
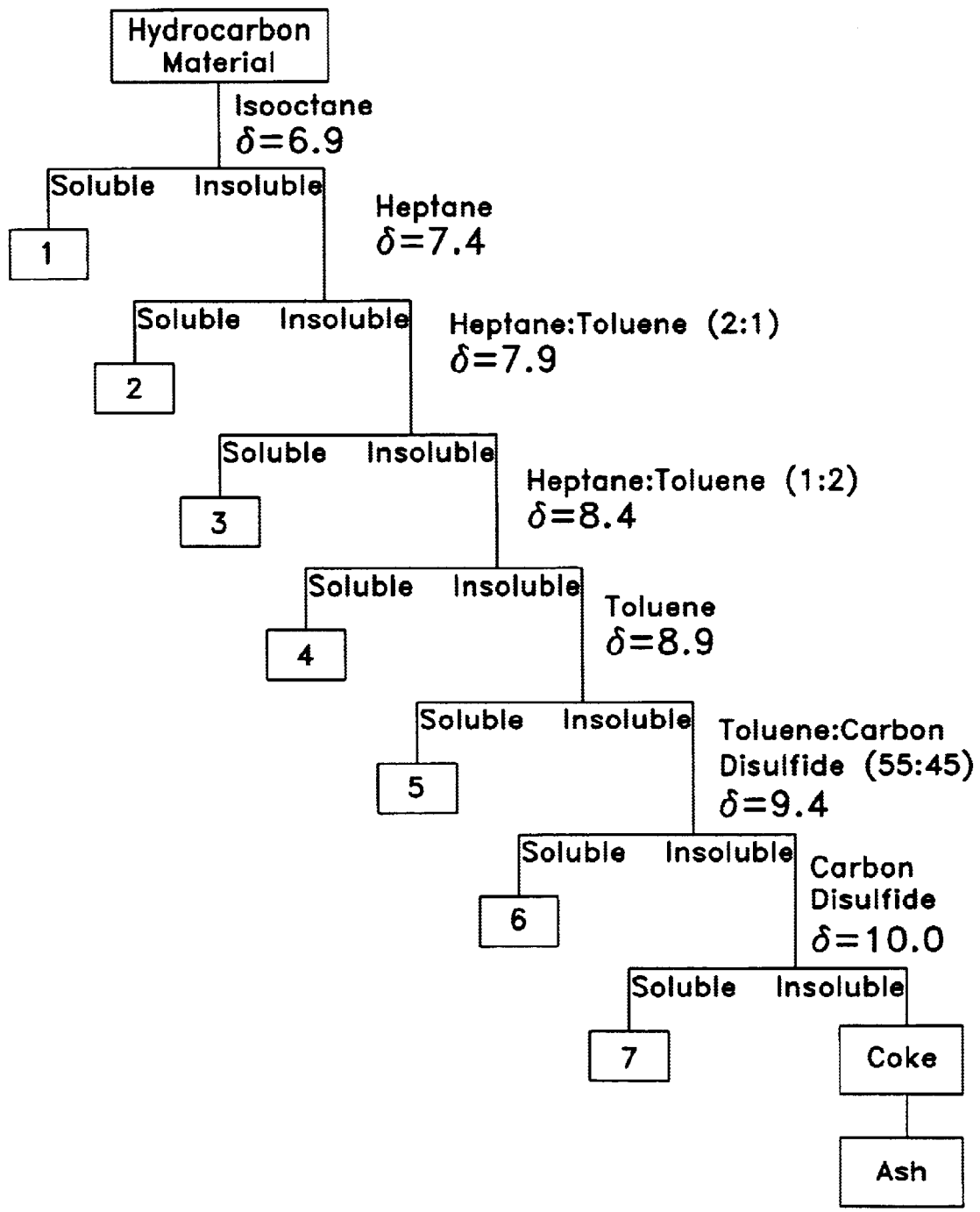
FIG. 3 shows a flow diagram of the hydrocarbon material solvent extraction sequence and solubility parameters of solvents.
Figure 4:
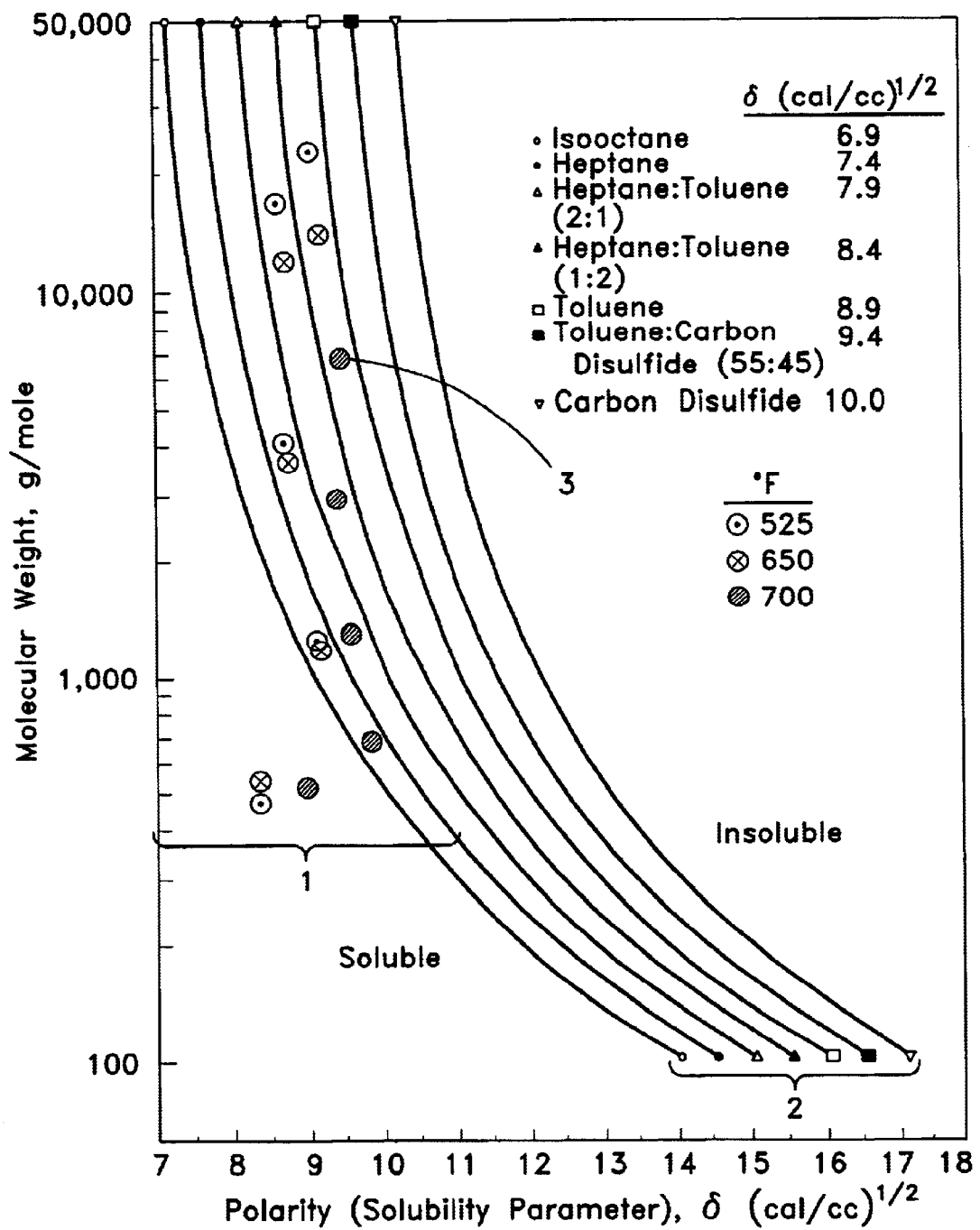
FIG. 4 shows a molecular weight polarity map.

Now referring to FIGS. 3 and 4, and the above discussion, an embodiment of the invention can be a molecular weight—polarity map developed specifically for hydrocarbon material components. A molecular weight—polarity map can have a first axis having values relating to molecular weight. It may also have a second axis having values relating to solubility parameter. As can be understood, a particular molecule or associated specie in a hydrocarbon material occupies a single point, or molecular weight—polarity coordinate location (3) on, on the map. A mixture of molecules or mixture of molecules with associated species forming a continuum of polarity or apparent molecular weight values or a combination of both (either of individual molecules or individual molecules with associated species) can be visualized as occupying a particular area on the map. For a particular solvent, the solubility of a solute increases with decreasing polarity, decreasing apparent molecular weight, or a combination of the two. As a hydrocarbon material undergoes thermal alteration, solvent perturbation, or aging, the changes in the molecules or associated species can cause the points representing these materials to move to a different region of the map. This movement can illustrate at least one unimodal characteristic of hydrocarbon materials. Interestingly, the core material can comprise a variably adjustable core material having a molecular weight responsive to temperature change. Also, it is important to note that the core material may have polarity which is stabilized within a region of solubility even when the molecular weight may change. Thus, such a map can be used as a means of evaluating the characteristics of hydrocarbon materials or diagnosing processing conditions or the state of thermal degradation. It can also be used as a tool in efforts to diagnose and possibly intervene in the incipient precipitation of polar materials during hydrocarbon material processing.

One embodiment of the phase diagram map can be developed by calculating the core material solubility regions, including the solubility region of asphaltenes, by determining solubility of core materials or asphaltenes in a variety of solvents. For example, solvents ranging from iso-octane, with a solubility parameter of 6.9 $(cal/cc)^{1/2}$, to carbon disulfide, with a solubility parameter of about 10.0 $(cal/cc)^{1/2}$. As shown by FIG. 4, the core material solubility region (1) can comprise between about 6.9 $(cal/cc)^{1/2}$ to about 11.0 $(cal/cc)^{1/2}$. The map can be based on solubility-parameter-tuned solvent mixtures providing even spacing between a plurality of solvent tuned contour lines (2) of about 0.5 $(cal/cc)^{1/2}$, except for the last series between toluene: $CS_2$ (55:45)(v:v) and $CS_2$, where the spacing can be 0.6 $(cal/cc)^{1/2}$. The border between the soluble and insoluble regions is defined arbitrarily as the solubility of a mole fraction of 0.001 (0.1%, or 1,000 ppm). This border is actually a point on a solubility gradient, where solubility increases towards the left-hand portion of a curve and decreases to the right. Naturally, other solvents or combinations of solvents could be used to create a range of solubility parameters having a different number or spacing with respect to the solvent tuned contour lines. As shown by FIG. 4, a particular embodiment of the molecular weight—polarity map can be established by using a first solvent tuned contour line based on iso-octane, a second solvent contour line based on heptane, a third solvent tuned contour line based on heptane:toluene (2:1)(v:v), a fourth solvent tuned contour line based on heptane:toluene (1:2)(v:v), a fifth solvent tuned contour line based on toluene, a sixth solvent tuned contour line based on toluene:carbon disulfide (55:45) (v:v), and an eighth solvent tuned contour line based on carbon disulfide.

The molecular weight—polarity related coordinate location (3)(for clarity not all the coordinate locations have leaders and identification numbers) of a particular material on the map was determined by three measurements. First, a solubility or solvent spectrum of the material was obtained to determine between what lines on the map the material lies. This was accomplished by performing a series of solubility measurements in a series of solvents of increasing or decreasing solubility parameters and determining their weight percentages of the soluble material. Excess solvent to solute (40:1 v:w) ratios were used to minimize any potential effect of the solute on the overall solubility parameter of the system. Second, a number average molecular weight of the molecules or associated species mixture was determined on the isolated fractions using vapor pressure osmometry in toluene at 60° C. Third, the isolated fractions were analyzed using analytical-scale size exclusion chromatography.

Ideal materials for demonstrating how the molecular weight—polarity map invention may apply to thermally treated hydrocarbon material having unimodal characteristics are bench-scale stripper bottoms oils (although the example is not meant to reduce the scope of invention to such materials or to such scale) which were generated as listed below:

A. Stripper Bottoms–273° C. (525° F.)
B. Stripper Bottoms–343° C. (650° F.)
C. Stripper Bottoms–371° C. (700° F.)

These three stripper bottom represent a series of increasing severity of thermal treatment at atmospheric pressure for the same hydrocarbon material. In the sequence of increasingly severe treatment, the A bottoms were fed into the B unit, whose bottoms were fed into the C unit These particular materials were allowed to remain in the strippers as they cooled down. Both Materials A and B were fully soluble in toluene, while Material C contained 13.5 weight percent toluene insoluble material, which yielded 17.9 weight percent ash results for the fractions are listed in Table 3. Portions of 150 $\mu$L of 0.2 weight percent solutions of the fractions were injected (0.3 mg). The values are reported relative to polystyrene standards having known molecular weight analyzed under the same conditions. As such, the standards must be used with caution since polystyrene and the hydrocarbon material or residua components are different materials.

The compiled data for the three stripper bottoms materials are presented in Table 2. Again referring to FIG. 4, the molecular weight—polarity map invention developed from the data and the effects of the thermal treatment on the three heavy oils prior to and during coke formation. The molecular weight—polarity map invention "peels" the layers of association with respect to a hydrocarbon material having unimodal characteristics. The gravimetric data show the progression towards more polar species as the severity of thermal treatment increases. Material C is generating both carbon or coke, or carbon or coke precursors (Fractions 6 and 7).

TABLE 2

Solubility Map Data for Three Stripper Bottoms

| Sample | | Fraction (See FIG. 3.) | | | | | | | | |
|---|---|---|---|---|---|---|---|---|---|---|
| Measurement | | 1 | 2 | 3 | 4 | 5 | 6 | 7 | coke | ash |
| A | Weight Percent | 85.9 | 0.8 | 6.3 | 5.1 | 0.7 | 1.1 | 0.1 | <0.1 | <0.1 |
|   | VPO Mn g/mole | 474 | 1260 | 4040 | 17000 | 23000 | — | — | — | — |
|   | $\delta$ (cal/cc)$^{1/2}$ | 8.4 | 9.2 | 8.8 | 8.8 | 9.2 | — | — | — | — |
| B | Weight Percent | 83.4 | 0.9 | 6.7 | 5.5 | 1.0 | 2.2 | 0.1 | 0.2 | <0.1 |
|   | VPO Mn g/mole | 542 | 1180 | 3580 | 12000 | 14000 | — | — | — | — |
|   | $\delta$ (cal/cc)$^{1/2}$ | 8.4 | 9.2 | 8.8 | 8.8 | 9.2 | — | — | — | — |
| C | Weight Percent | 64.0 | 2.0 | 5.3 | 5.8 | 2.9 | 4.5 | 1.5 | 11.5 | 2.5 |
|   | VPO Mn g/mole | 516 | 684 | 1320 | 2920 | 6800 | — | — | — | — |
|   | $\delta$ (cal/cc)$^{1/2}$ | 9.0 | 9.9 | 9.6 | 9.5 | 9.5 | — | — | — | — |

With respect to the first measurement, as discussed above and now referring to FIG. 3, a solubility or solvent spectrum of the material was obtained using the solvent extraction sequence illustrated. All solvents used were reagent grade or better from commercially available sources. Iso-octane asphaltenes were first obtained by heating the whole residua with a 40:1 (v:w) portion of iso-octane to about 70° C. for 1 hour with stirring. The mixture was stirred at room temperature overnight, then allowed to set for at least 0.5 hour prior to vacuum filtering through a medium frit (10–15 $\mu$m) sintered glass filter. To remove solvent from the insolubles, air was passed through the filter for 5 min, they were placed in a vacuum oven at 120° C. and 23 inches Hg vacuum for 1 hour, were cooled, then weighed. A 40:1 ratio (v:w) of n-heptane was mixed with the insolubles and stirred overnight. The insolubles were filtered using vacuum filtration through a medium glass filter. These steps were repeated with the series of solvents shown in FIG. 4. At the end of the series, the carbon disulfide insolubles (including coke) were ashed in a muffle furnace at 400° C. overnight to obtain weight percent ash With respect to the second measurement, number average molecular weights were determined with a Knaur vapor pressure osmometry (VPO) instrument using toluene at 60° C. (ASTM D-2503). Determinations were made with 1–4 weight percent sample solutions. Benzil was used for calibration.

With respect to the third measurement, high-performance analytical scale size exclusion chromatography (SEC)

The data also show that the number average molecular weights of the iso-octane-soluble maltenes are about the same for all three oils. The molecular weight of each of the more polar fractions decreases significantly with thermal treatment. The main difference between the various polar fractions for a particular material seems to be molecular weight The solubility parameters are similar for a particular series of polar materials with large differences in apparent molecular weight. This leads to the speculation that a residua colloidal system self-adjusts to lower the overall energy of the system by matching as closely as possible the polarity of the associated complexes to the solvent matrix (iso-octane maltenes). This appears to occur by automatic adjustment of the apparent molecular weights of the complexes.

For the pyrolysis series, the higher molecular weights are probably due to associated species, which the thermal treatment is breaking apart. This results in an overall less stable colloidal-type system with increasing severity of thermal treatment, as was observed with the Heithaus titration data discussed below. Also, significant cracking has taken place in Material C, which further reduces the apparent molecular weight of the corresponding factions soluble in the various solvents compared to Materials A and B. The solubility parameters (polarities) of the fractions from C are larger than the corresponding fractions from A and B. The data clearly show some significant differences between Material C, and the less severely treated Materials A and B.

TABLE 2

High-Performance Size Exclusion Chromatography Results

| Fraction | Size Exclusion Chromatography | | | | VPO |
|---|---|---|---|---|---|
| | Mw | Mn | Range[a] | Mw/Mn | Mn |
| A (273° C./525° F.) | | | | | |
| 1 | 928 | 422 | 210–2200 | 2.20 | 474 |
| 2 | 1490 | 585 | 270–3400 | 2.55 | 1260 |
| 3 | 2440 | 772 | 340–5600 | 3.16 | 4040 |
| 4 | 2240 | 618 | 260–5400 | 3.62 | 17000 |
| 5 | 2120 | 523 | 210–5300 | 4.05 | 23000 |
| B (343° C./650° F.) | | | | | |
| 1 | 923 | 439 | 220–2100 | 2.10 | 542 |
| 2 | 1320 | 539 | 250–3000 | 2.45 | 1180 |
| 3 | 2110 | 703 | 310–5000 | 3.00 | 3580 |
| 4 | 2090 | 611 | 260–5000 | 3.42 | 12000 |
| 5 | 1930 | 510 | 210–4800 | 3.78 | 14000 |
| C (371° C./700° F.) | | | | | |
| 1 | 705 | 395 | 210–1500 | 1.78 | 516 |
| 2 | 788 | 388 | 190–1800 | 2.03 | 684 |
| 3 | 1140 | 481 | 220–2600 | 2.37 | 1320 |
| 4 | 1350 | 516 | 230–3200 | 2.61 | 2920 |
| 5 | 1230 | 455 | 200–2900 | 2.70 | 6800 |

[a]From elution volumes at 10% to 90% of peak area

Except for the number average molecular weight values for the extracted iso-octane maltenes for all three materials (Fraction 1), the values are significantly lower than the number average molecular weight values determined by VPO. The discrepancy cannot be wholly attributed to the use of polystyrene standards and the non-uniform response with refractive index detection from residua components of differing functionality. Some adsorption of materials on the polystyrene-divinylbenzene stationary phase may be occurring also. The values determined by VPO represent the apparent number average molecular weights in 1–4 weight percent toluene solutions. An additional possible effect may be that associative complexes that give apparent high VPO molecular weight values in solution break down during the SEC separation for Fractions 4–5 for all three materials, resulting in significantly lower apparent number average molecular weight values than the corresponding VPO values. To check this further, various amounts of one of the fractions for which sufficient material was available were injected onto the high-performance SEC column. The fraction was Material A, Fraction 4 which gave an apparent VPO molecular weight of 17,000 g/mole and a SEC number average molecular weight of 618 g/mole (Table 2).

Figure 5:
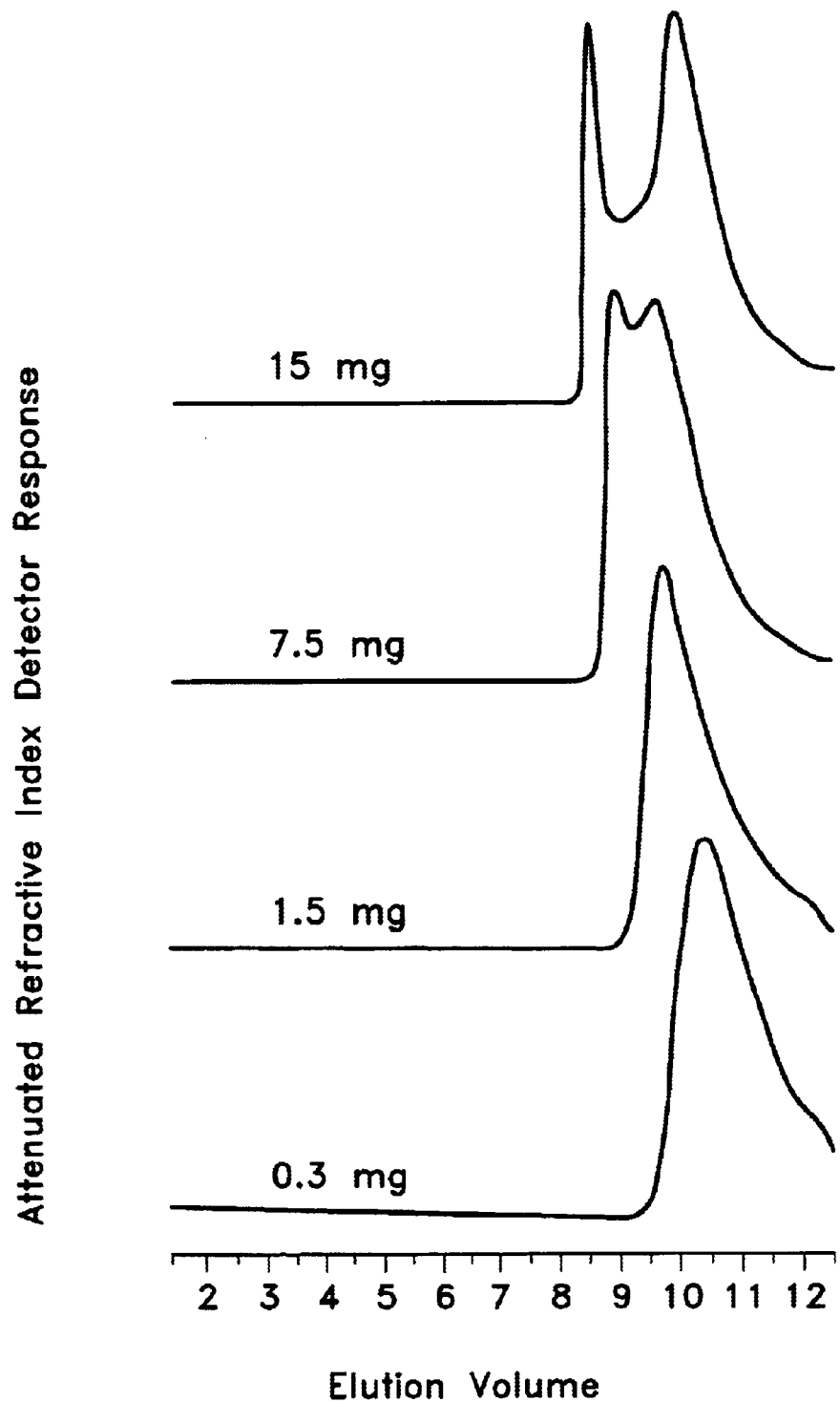
FIG. 5 shows elution profiles of high performance size exclusion chromatography of various amounts of material A from fraction 4.

Now referring to FIG. 5, which shows the results from injections of 100 µL of toluene solutions containing 0.3–15 mg onto the SEC column. As more material was injected, the retention volume decreased, indicating an increase in associations or apparent molecular weight. For the 7.5 mg injected, the peak split into two peaks, suggesting the presence of significant associations. This peak splitting and elution volume shortening phenomenon was not observed when a polystyrene standard with a molecular weight of 400 g/mole was injected under identical conditions. Thus, the peak splitting phenomenon is not likely due to overloading the column with sample. For injections of 0.3 to 7.5 mg, the material eluted in about 3 mL of toluene. The concentration at which significant complex formation begins for this asphaltenic material is estimated to be at the point where the peak splits. This occurs somewhere between 1.5 and 7.5 mg injected diluted into about 3 mL toluene elution solvent, which is between about 0.06–0.3 weight percent. This result may be consistent with the results of Andersen and Birdie, who reported a critical micelle concentration of asphaltenes in toluene near 0.38 weight percent using calorimetric titration. Andersen, S. I. and K. S. Birdi, *Aggregation of Aphaltenes as Determined by Calorimetry*, Journal of Colloid and Interface Science, 142, pp. 497–502 (1991).

As can be understood from the table, as with the VPO data, the SEC number average molecular weights for a particular fraction generally decrease with increasing severity of thermal treatment. The polydispersity Mw/Mn, an indicator of molecular weight distribution, also decreases for a particular fraction with increasing severity of thermal treatment.

Figure 6:
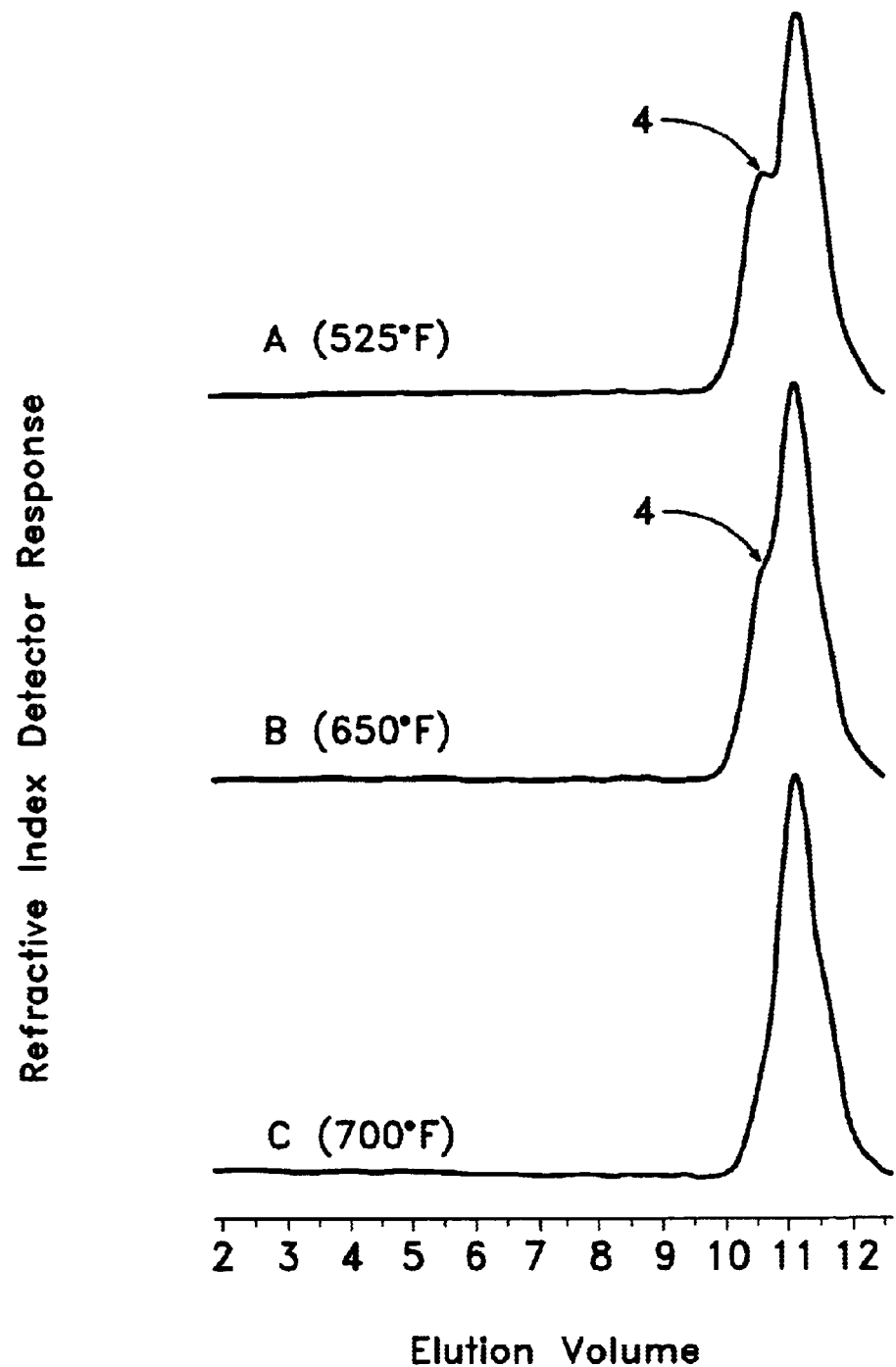
FIG. 6 shows elution profiles of high performance size exclusion chromatography of maltenes.

Now referring to FIG. 6, chromatograms appeared as essentially symmetrical peaks with one exception—the iso-octane maltenes (Fraction 1). These chromatograms show a leading high molecular weight shoulder component (4) in the 273° C. (525° F.) material, which was smaller for the 343° C. (650° F.) material and was not evident for the 371° C. (700° F.) material. As such, this component of the iso-octane maltenes having an apparent high molecular weight appears to be related to at least one unimodal characteristic of hydrocarbon materials which can be destroyed with increasing severity of thermal treatment.

An embodiment of the invention based on this finding comprises an indicia of stability$_{USC}$ based upon the steps of detecting this unimodal characteristic stability component having apparent high molecular weight This approach may comprise providing a hydrocarbon material component analysis device, or devices in combination, which can be a size exclusion chromatography device as described above, or could also be other devices for identifying the apparent high molecular weight unimodal stability component such as a mass spectrometry device, an infrared spectrometry device, a raman spectroscopy device, gel phoresis device, paper chromatography device, or nuclear magnetic resonance device. Naturally, each hydrocarbon analysis device could be configured, as would be well known to those of skill in the art, so that the unimodal characteristic stability component could be identified. While in the example above, maltenes were extracted into iso-octane, other solvents, or other devices could be used to isolate the corresponding maltenes containing the unimodal characteristic stability component from the hydrocarbon material. Thereafter, detection of the unimodal stability component could comprise observing elution of the apparent molecular weight of the unimodal characteristic stability component directly as described above for size exclusion chromatography where the apparent molecular weight can be equal to or larger than about 500 gram per mole. As the amount of the unimodal characteristic stability component approaches zero continued thermal processing results in carbon deposition including coke formation.

Figure 7:
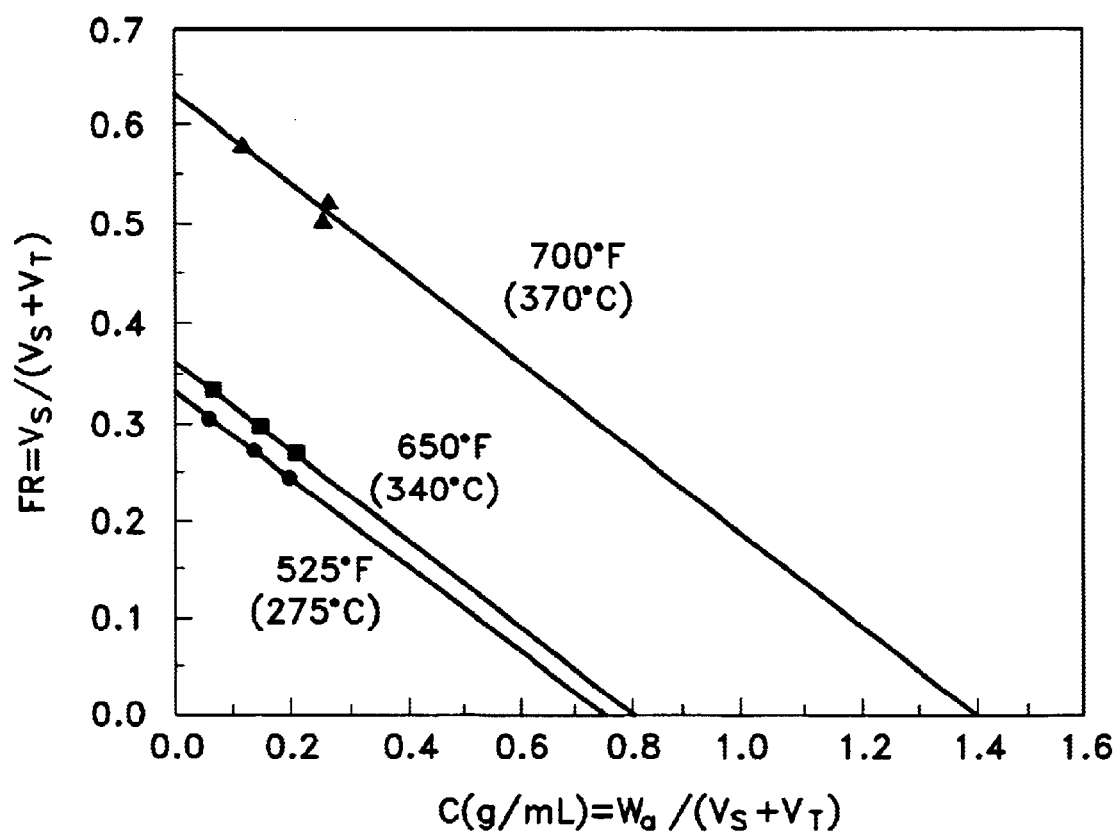
FIG. 7 shows titration results for three stripper bottoms.

Now referring to FIG. 7, in addition to the above-mentioned three measurements, automated Heithaus titration was performed with the toluene-soluble components of hydrocarbon material (although other dissolvents could be used such as benzene, xylene, ethylbenzene, similar aromatic hydrocarbons). This method comprises preparing three toluene solutions at different concentrations of hydrocarbon material. Each can be titrated with a weak solvent such as iso-octane (although other weak solvents could be used such as pentane, hexane, heptane, hexadecane, or similar aliphatic hydrocarbons) with a titration device. The weight of residua or asphalt ($W_a$), the volume of toluene ($V_s$), and volume of iso-octane titrant ($V_t$) are recorded at the flocculation point where asphaltenes just begin to precipitate for each solution. The flocculation ratio and dilution concentration are calculated as follows:

FR=Flocculation Ratio=$V_s/(V_s+V_t)$

C=Dilution Concentration=$W_a/(V_s+V_t)$

A plot of FR versus C can be made and the intercepts determined ($FR_{max}$ and $C_{min}$). The Heithaus parameters are defined as follows:

| | |
|---|---|
| $p_a = 1 - FR_{max}$ | Peptizability of Asphaltenes |
| $p_o = FR_{max} \times (1/C_{min} + 1)$ | Solvent Power of Maltenes |
| $P = p_o/(1 - p_a) = 1/C_{min} + 1$ | Overall Compatibility of Residua |

Larger values of $p_a$ may indicate more peptizable asphaltenes, and larger values of P indicate an overall compatible system. A larger $p_o$ value is subject to a mixed interpretation.

The Heithaus parameters for these three stripper bottoms materials are provided in Table 4. The results show that the three bottoms materials are becoming less stable with increasing severity of thermal treatment The results also show a significant difference between Material C, which is producing coke or carbonaceous material, and Materials A and B, which are not yet near coke production or carbon deposition.

TABLE 4

Heithaus Titration Results for Three Stripper Bottoms

| | Material | | |
|---|---|---|---|
| Heithaus Parameter | A (525° F.) | B (650° F.) | C (700° F.) |
| $p_a$ | 0.668 | 0.638 | 0.364 |
| $p_o$ | 0.766 | 0.805 | 1.09 |
| P | 2.31 | 2.23 | 1.71 |
| $p_a/C_{min}$ Ratio | 0.87 | 0.78 | 0.26 |

Another way of evaluating $FR_{max}$ can be that it is the volume fraction of toluene in a toluene- iso-octane mixture, assuming additive volumes. By knowing the solubility parameter of both solvents, the solubility parameter at $FR_{max}$ can be calculated. $FR_{max}$ is thus a measure of the solubility parameter at infinite dilution at which asphaltenes begin to precipitate. Such measurements also may have applicability in predicting precipitation of asphaltenes for mixtures of two or more residua. A relatively larger $FR_{max}$ indicates a less soluble asphaltene. Since solubility depends on both molecular weight and polarity, this can be due to a higher molecular weight or more polar asphaltene, or both $C_{min}$ is the ratio of residua to titrant (iso-octane for this example although other solvents can be used) at which asphaltenes begin to precipitate. A larger $C_{min}$ indicates a less compatible system (smaller P). Assuming that asphaltene flocculation occurs at a particular solubility parameter for a particular residua, it is apparent that both $FR_{max}$ and $C_{min}$ and the line connecting them are at the same solubility parameter.

The solubility parameter at which asphaltenes begin to precipitate (at $FR_{max}$) and the solubility parameters of the residua matrix (at $C_{min}$) were calculated and are listed in Table 5 for the three stripper bottoms. Both the solubility parameter for the whole residua and the solubility parameter of the onset of asphaltene flocculation increase with increasing severity of thermal treatment. The material that has been heated to the point of coke production is significantly more polar than the same material prior to coke production. This is also reflective of cracking and the removal of less polar distillates with heating.

TABLE 5

Solubility Parameters for Whole Residua and Asphaltene Precipitation Onset

| | Solubility Parameter, δ (cal/cc)$^{1/2}$ | |
|---|---|---|
| Material | Whole Residua | Asphaltene Precipitation Onset |
| A (525° F.) | 8.4 | 7.6 |
| B (650° F.) | 8.5 | 7.6 |
| C (700° F.) | 9.1 | 8.2 |

Now referring to Table 4, another embodiment of the invention based on the titration data provides an indicia of stability defined as $p_a/C_{min}$. This indicia of stability$_{pa/Cmin}$ can be based on the above described consideration that $p_a$ decreases and $C_{min}$ increases as the overall stability of the unimodal characteristics decreases. A threshold of instability$_{pa/Cmin}$ value for can be assigned at a value within the range of about 0.1 to about 0.4. The indicia of stability$_{pa/Cmin}$ for a particular hydrocarbon material can be compared to the threshold of instability$_{pa/Cmin}$. As can be understood for residuum C in Table 4 the $p_a/C_{min}$ has decreased from a value of 0.87 to a value of 0.26. The first value indicative of a relatively stable hydrocarbon material having unimodal characteristics while the second value suggests that the material has acquired some degree of multimodal character, which may include the formation of coke.

Now referring to Table 6, another embodiment of the invention can be an indicia of stability based upon determining the amount of precipitated asphaltenes which are soluble in a solvent having a polarity between that of the precipitating solvent and a solvent which can dissolve the precipitated asphaltenes completely. For the three stripper bottoms, as an example, asphaltenes were precipitated using heptane, although other precipitating solvents can be used including iso-octane, pentane, or hexane for example. The precipitated asphaltenes can then extracted with a second solvent, in this example cyclohexane, having polarity that is between the precipitating solvent and a polarity which would substantially dissolve the precipitate completely. Other solvents could be used as the second solvent depending on which solvent was used as the precipitating solvent such as pentane, heptane, or heptane: toluene 1:1 (v:v).

TABLE 6

Solubility of Heptane Asphaltenes in Two Solvents with δ = 8.2 (cal/cc)½

| | wt. % Heptane | wt. % Asphaltenes Soluble in: | |
|---|---|---|---|
| Material | Asphaltenes | Cyclohexane | Heptane: toluene (1:1) (v:v) |
| A (525° F.) | 11.9 | 14.0 | 63.2 |
| B (650° F.) | 14.2 | 10.8 | 52.4 |
| C (700° F.) | 22.4 | 1.8 | 26.9 |

As can be understood from Table 6, both hydrocarbon materials A and B are fully soluble in cyclohexane, yet the heptane asphaltenes are only partially soluble. Again, this is due to the associated unimodal nature of these materials. The cyclohexane-soluble components of the asphaltenes can reflect the state of the solubilizing resins in these materials. The disappearance of the cyclohexane-soluble portion of heptane asphaltenes as the stripper bottoms are increasingly heated is illustrated by the data for the stripper bottoms and appears to coincide with acquired multimodal characteristics, including coke formation. As such, an indicia of stability reflects an observed amount of precipitated asphaltenes soluble in the second solvent.

It is interesting to note that the solvent mixture heptane:toluene (1:1)(v:v), which has the same solubility parameter as cyclohexane, (8.2 (cal/cc)$^{1/2}$), gives a larger yield of soluble material than cyclohexane from the heptane asphaltenes for each of the three stripper bottoms. A likely explanation is that in addition to the solubility parameter, there is a chromatographic effect due to the presence of toluene in the mixed solvent. Possibly toluene is displacing some associated material from the associated asphaltene complex. Although solubility parameters of mixtures are additive with the volume fractions of the components, chromatographic solvent strengths are not. The first small portion of a stronger chromatographic solvent in a mixture with a weaker one increases the overall chromatographic solvent strength almost exponentially. This is a plausible explanation of the data in Table 6. This also provides additional evidence for the presence of associated species in a hydrocarbon material having unimodal characteristics.

Again referring to Table 6, another embodiment of the invention can comprise an indicia of stability$_{y/x}$ be established by determining the weight percent asphaltenes soluble in the second solvent (Y) to the weight of the asphaltenes precipitated by the first solvent (X). A larger weight percent asphaltene would indicate a greater coking tendency, as would a smaller weight percent soluble portion of the asphaltenes. A threshold of instability$_{y/x}$ can be assigned a value of between about 0.0 to about 1.0. The indicia of stability$_{y/x}$ can be compared to the threshold of instability$_{y/x}$ to determine the proximity of a hydrocarbon material to acquiring multimodal characteristics. The ratio values for the three stripper bottoms are 1.2, 0.76, and 0.08 for the materials treated at 273, 343, and 371° C. (525, 650, and 700° F.), respectively. The proximity of the hydrocarbon to acquiring multimodal characteristics, including coke formation, is closer as the value for this indicia of stability approaches zero.

To further define aspects of the unimodal character of hydrocarbon materials, and illustrate the universal applicability of the above-described indicia of stability, thresholds of instability, or their application to assessing proximity of the unimodal characteristics to acquisition of multimodal characteristics, including carbon deposition or coke formation, five additional hydrocarbon materials were evaluated. These petroleum residua were Boscan, California Coastal MaxCL, Redwater, B. C., and Vistar. While these particular residua were the focus of the following examples, their choice is not intended to limit the application of the described embodiments of the invention solely to such hydrocarbon materials. Embodiments of the invention may have application over a broad range of hydrocarbon materials such as other petroleum residua, heavy oils, coal tars, shale oils, asphalts, or the like.

Figure 8:
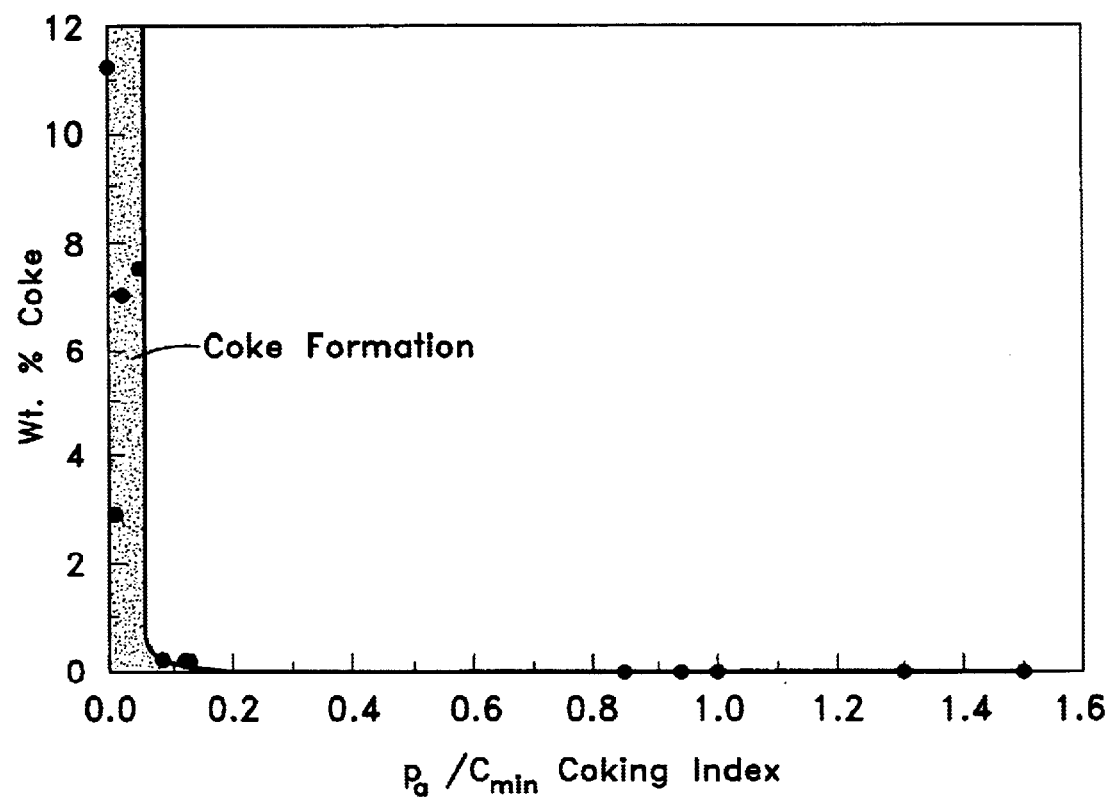
FIG. 8 shows weight percent coke relative to values for the indicia of stability$_{pa/Cmin}$.
Figure 9:
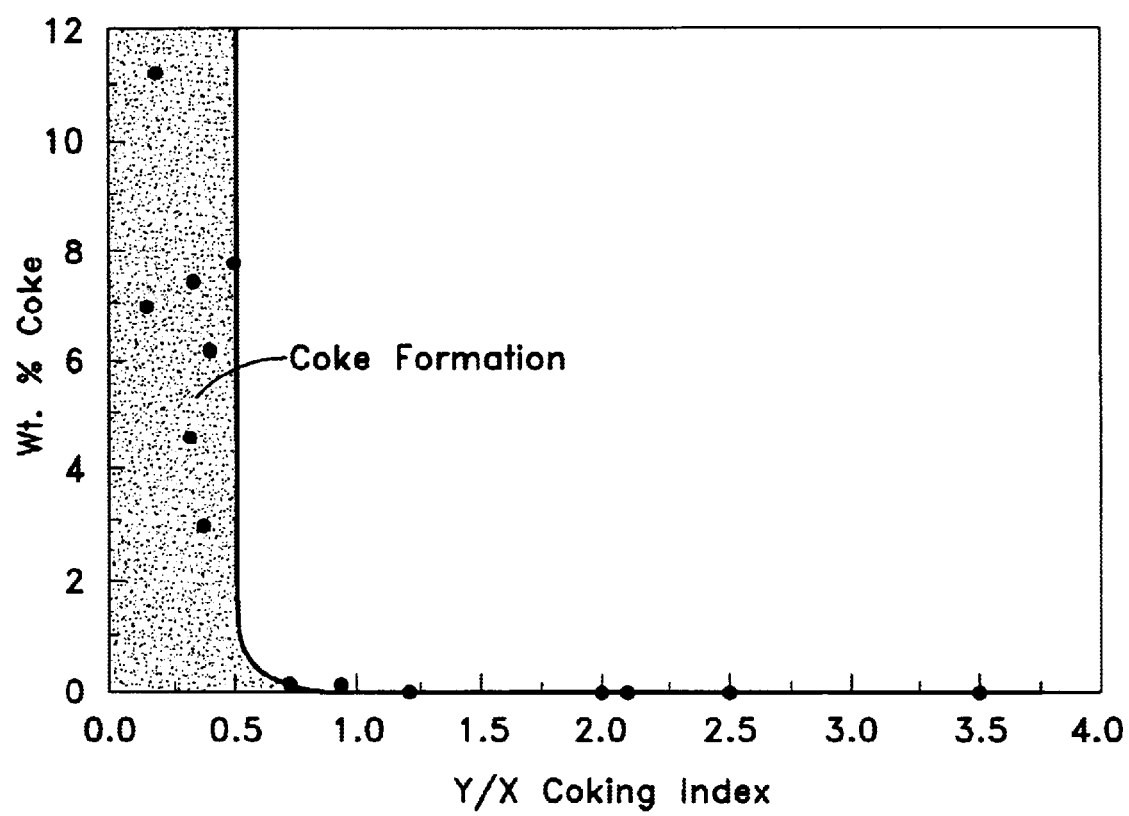
FIG. 9 shows weight percent coke relative to values for the indicia of stability$_{y/x}$ based upon the weight percent of precipitated asphaltenes soluble in a second solvent over the weight percent of precipitated asphaltenes.

Now referring to FIGS. 8 and 9, and Tables 7 and 8, indicia of stability$_{pa/Cmin}$, and indicia of stability$_{y/x}$ from the cyclohexane soluble portions of precipitated asphaltenes for the five hydrocarbon materials are illustrated. For these determinations, hydrocarbon materials were pyrolyzed at 400° C. for 60 and 90 minutes. Pyrolysis experiments were conducted in a stirred batch reactor system constructed from 4-inch diameter stainless steel pipe charged with about 120 g of hydrocarbon material. The reactor was heated to the desired set point temperature (400° C.) and held at that temperature for the duration of the experiment At the end of the experiment, the reactor was allowed to cool and the contents of the reactor were recovered. The carbon solids or coke can be separated from the product oil by solubility in toluene.

The amount of carbon solids formed at both 60 and 90 minute residence times was evaluated in terms of the above mentioned indica of stability. Heithaus titrations could not be performed on the 90 minute pyrolysis products because of sample instability and the immediate formation of precipitate in the titration cells. Therefore, the $p_a/C_{min}$ embodiment of indica of instability was not determined for the 90 minute products.

TABLE 7

Heithaus Titration Results and $p_a/C_{min}$ Indicia of Stability

| Material | $p_a$ | $p_o$ | P | $C_{min}$ | $p_a/C_{max}$ |
|---|---|---|---|---|---|
| Redwater, B.C. | | | | | |
| Original | 0.698 | 0.749 | 2.48 | 0.676 | 1.0 |
| Pyrolyzed 60 min. | 0.422 | 0.753 | 1.30 | 3.19 | 0.13 |
| Pyrolyzed 90 min. | 0.162 | 0.878 | 1.05 | 21.1 | 0.0076 |
| CA Coastal | | | | | |
| Original | 0.614 | 1.12 | 2.89 | 0.529 | 1.2 |
| Boscan | | | | | |
| Original | 0.691 | 0.992 | 3.21 | 0.452 | 1.5 |
| Pyrolyzed 60 min. | 0.245 | 0.905 | 1.20 | 5.00 | 0.049 |
| Pyrolyzed 90 min. | 0.285 | 0.717 | 1.00 | 434 | 0.00 |
| MaxCL | | | | | |
| Original | 0.682 | 0.758 | 2.38 | 0.725 | 0.94 |
| Pyrolyzed 90 min. | 0.152 | 0.973 | 1.15 | 6.80 | 0.022 |
| Vistar | | | | | |
| Original | 0.616 | 0.916 | 2.38 | 0.722 | 0.85 |
| Pyrolyzed 60 min | 0.373 | 0.831 | 1.32 | 3.08 | 0.12 |

As can be understood from FIG. 8, as indicia of stability$_{pa/Cmin}$ approaches about 0.1 the unimodal character of the hydrocarbon material becomes unstable which may be accompanied by carbon deposition or coke formation.

TABLE 8

Heptane Asphaltenes and Asphaltenes Soluble in Cyclohexane

| | Weight Percent | | | Wt. % |
|---|---|---|---|---|
| Residuum | X: Heptane Asphaltenes[a] | Y: Asphaltenes Soluble in Cyclohexane | Y/X | Toluene Insolubles (Coke) |
| Redwater, B.C. | | | | |
| Original | 11.7 | 41.4 | 3.5 | <0.01 |
| Pyrolyzed | | | | |
| 60 min. | 15.9 | 14.7 | 0.92 | 0.2 |
| 90 min. | 17.1 | 6.0 | 0.35 | 2.9 |
| CA Coastal | | | | |
| Original | 19.7 | 23.1 | 1.2 | <0.01 |
| Pyrolyzed | | | | |
| 60 min. | 13.9 | 4.5 | 0.32 | 4.4 |
| 90 min. | 11.6 | 5.7 | 0.49 | 7.9 |
| Boscan | | | | |
| Original | 19.8 | 40.6 | 2.1 | <0.01 |

TABLE 8-continued

Heptane Asphaltenes and Asphaltenes Soluble in Cyclohexane

| Residuum | Weight Percent | | Y/X | Wt. % Toluene Insolubles (Coke) |
|---|---|---|---|---|
| | X: Heptane Asphaltenes[a] | Y: Asphaltenes Soluble in Cyclohexane | | |
| Pyrolyzed | | | | |
| 60 min. | 15.6 | 5.3 | 0.34 | 7.5 |
| 90 min. | 12.5 | 2.6 | 0.21 | 11.2 |
| MaxCL | | | | |
| Original Pyrolyzed | 18.1 | 45.8 | 2.5 | <0.01 |
| 90 min | 19.8 | 3.6 | 0.18 | 7.0 |
| Vistar | | | | |
| Original Pyrolyzed | 18.0 | 36.8 | 2.0 | <0.01 |
| 60 min. | 18.2 | 13.2 | 0.73 | 0.2 |
| 90 min. | 9.5 | 3.8 | 0.40 | 6.2 |

[a]Weight percent of toluene soluble material

Similarly it can be understood from FIG. 9, that indicia of stability$_{y/x}$ (weight percent of precipitated asphaltenes soluble in cyclohexane to asphaltenes soluble in heptane) (although other solvent pairs can be used as discussed above) approaches about 1.0 the hydrocarbon material becomes unstable which may be accompanied by carbon deposition or coke formation.

The plots dramatically illustrate the diagnostic potential of the indicia of stability and indicia of instability in measuring how close a hydrocarbon material may be to acquiring multimodal characteristics including carbon deposition such as coke formation.

Additional relationships, in addition to those described above, have also been considered in evaluating these hydrocarbon materials. As a result additional embodiments of the invention for evaluation of unimodal character of hydrocarbon materials have been delineated. As discussed above and in greater detail below hydrocarbon materials having unimodal characteristics can be considered to be a series of components functionally related by a continuum of polarity in which core materials such as polar asphaltene materials are dispersed in a solvent phase.

Extensive experimentation was conducted to create a theoretical model to analyze unimodal characteristics related to hydrocarbon material and their transition to multimodal characteristics. The experimentation was also directed to elucidate aspects of the theoretical model for unimodal character which could be practically measured or valued. The model focuses upon association of components in hydrocarbon materials. Resins and solvent layers associated about a core material of hydrocarbon materials such as asphaltene (although the core material may be other polar components of hydrocarbon materials or may include other components associated with the asphaltene), and solvated core materials interacting with each other in an ordered hydrocarbon material system. Additional solvent can be associated with or trapped between the solvated core material.

The model defines a hydrocarbon solvation shell magnitude term K ($K=K_S \cdot K_F$) representing the amount of solvent adsorbed around a core material such as an asphaltene ($K_S$) or the solvent associated with or trapped by a group of solvated core materials ($K_F$) in an ordered unimodal system.

For hydrocarbon materials such as the petroleum residua evaluated, K values ranging from 3–6 at 25° C. can be typical. As a hydrocarbon material is heated K decreases, indicating a decreasing amount of trapped solvent associated with the solvated core materials in the hydrocarbon material and flocculation of the core material may result. This may be a reversible process on cooling, unless pyrolysis reactions begin, at temperatures above 340° C. Solvation constants (K) are derived using:

$$K_S K_F \equiv K = \frac{1 - \eta_{rel}^{-0.4}}{\chi_n / 1.2}$$

In the equation, K is the overall solvation constant for the hydrocarbon material, $K_S$ is the ratio of the size of the solvated core material to the size of the core material itself, $K_F$ is the amount of solvent otherwise associated with the solvated core materials, $\chi_a$ is the mass fraction of heptane asphaltenes, divided by an assumed density of 1.2 grams per cubic centimeter to yield the size fraction of the core materials, and $\eta_{rel}$ is the relative viscosity. To estimate relative viscosities, core material precipitation with can be performed with a solvent such as heptane. Zero shear viscosities ($\eta$, cps) are measured for a hydrocarbon material and for the corresponding heptane maltenes (72 °, cps). The ratio of $\eta/\eta°$ is called the relative viscosity ($\eta_{rel}$) and is diagnostic of the manner in which core materials such as asphaltenes are suspended in a solution of maltenes. This value is somewhat dependent on the solvent used to precipitate the asphaltenes and is related to the state of peptization. A higher relative viscosity indicates a more significant unimodal characteristic. The effective core material volume faction, $\phi_{eff}$ is given by multiplying K by the volume fraction of heptane asphaltenes.

$$\phi_{eff} = K \chi_a / 1.2$$

Values of $K_S$ for a hydrocarbon material can indicate whether or not unimodal character is present The value of $K_S$ can depend on the experimental data used. For example, relative viscosities using heptane or iso-octane maltenes may vary somewhat Results from the determination of $K_S$ using more than one approach, for a wide selection of hydrocarbon materials having unimodal characteristics, show that for unpyrolyzed hydrocarbon material such as petroleum residua the typical value of $K_S$ is 1.6. With pyrolysis (>340° C.), there is a carbon deposition or coke induction period during which a multimodal system begins to form as discussed by Schabron, J. F., A. T. Pauli, and J. F. Rovani, Jr., *Petroleum Residua Solubility Parameter/ Polarity Map Stability Studies of Residua Pyrolysis*, WRI Report 99-R004 to DOE under Cooperative Agreement DE-FC26-98FT40322 (1999), hereby incorporated by reference. With continued pyrolysis, carbon deposition or coke begins to form as the unimodal characteristics have broken down irreversibly. When this occurs, relative viscosity measurements have no validity. Thus, to estimate $K_F$ and $K_S$ for pyrolyzed hydrocarbon materials, alternative calculations can be used. In these equations, $\chi_{cy}$ $$K_S = \frac{1}{1 - \chi_{cy}} \quad K_F = \frac{1}{1 - p_a}$$

is the weight fraction of heptane asphaltenes soluble in cyclohexane, and $p_a$ is the Heithaus parameter, each as described above.

Figure 10:
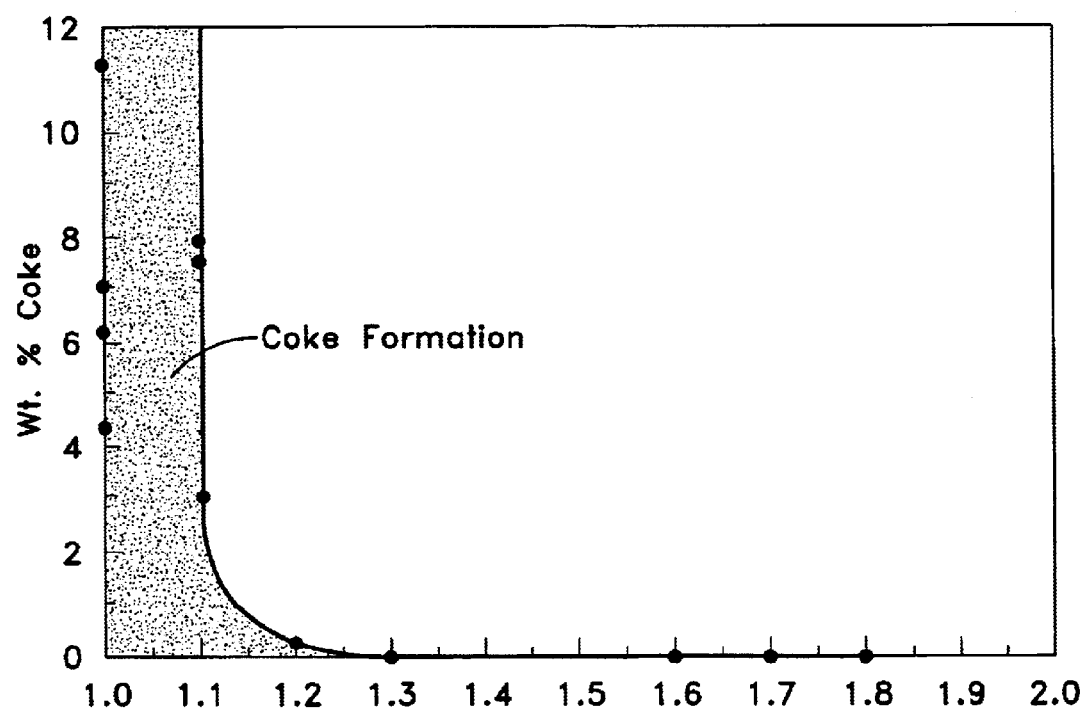
FIG. 10 shows weight percent coke relative to values for the indicia of stability$_{Ks}$.
Figure 11:
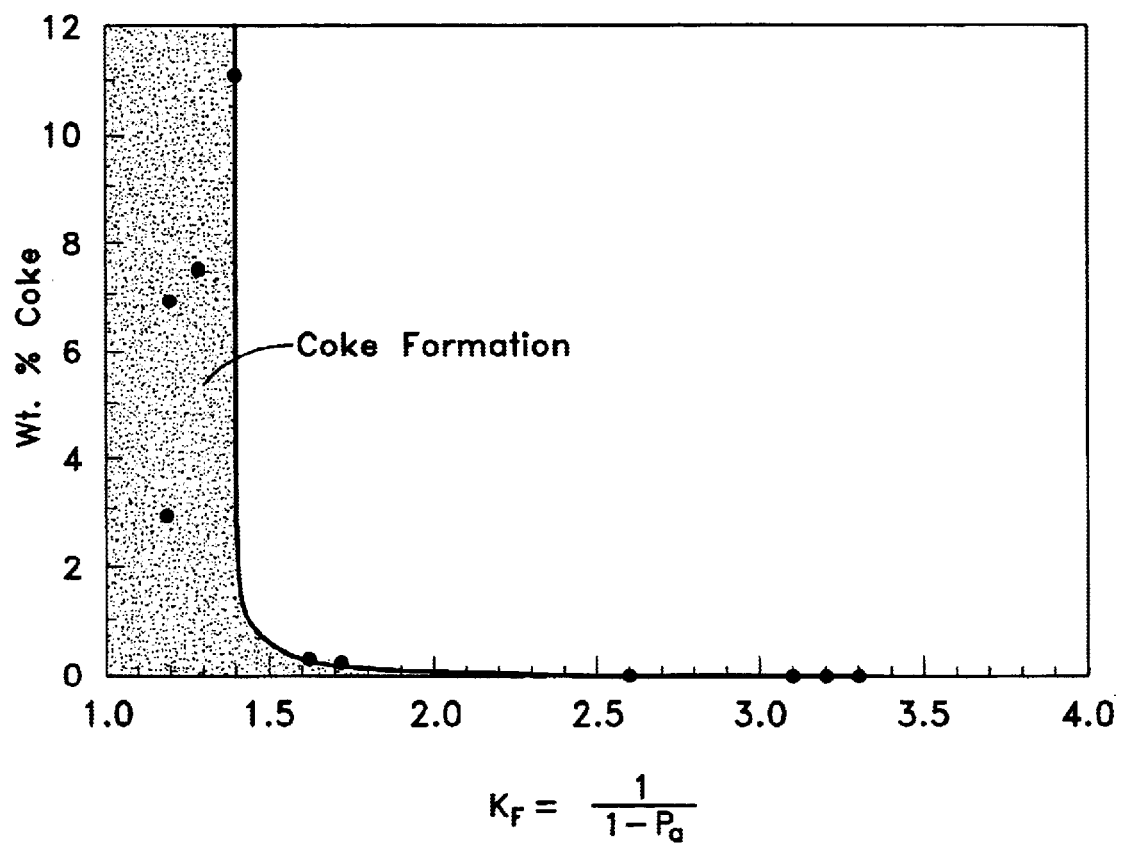
FIG. 11 shows weight percent coke relative to values for the indica of stability$_{KF}$.
Figure 12:
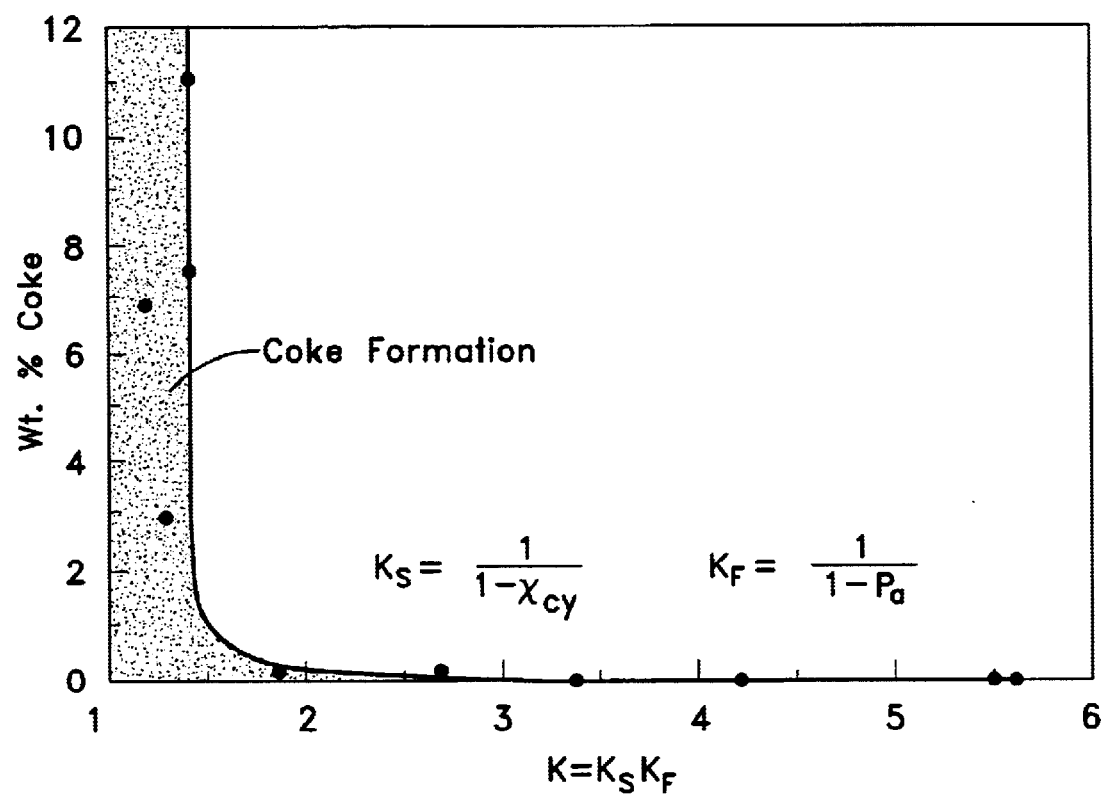
FIG. 12 shows weight percent coke relative to values for the indica of stability$_K$.

Now referring to FIGS. 10, 11, and 12, and Table 9, the theoretical basis for additional embodiments of the invention becomes evident when values for these terms are determined before and after pyrolysis at various severities. Table 9 lists the values of $K_S$, $K_F$, and $K$ and weight percent carbon deposition or coke for the five residua. The data are plotted in FIGS. 10, 11, 12, respectively.

TABLE 9

$K_S$, $K_F$, and $K$ values for the Original and Pyrolyzed Residua

| Residuum | $K_S =$ $(1/(1 - \chi_{cy}))$ | $K_F =$ $(1/(1 - p_a))$ | $K = K_S \cdot K_F$ | Toluene Insolubles (Coke)[a] |
|---|---|---|---|---|
| Redwater, B.C. | | | | |
| Original Pyrolyzed | 1.7 | 3.3 | 5.6 | <0.01 |
| 60 min. | 1.2 | 1.7 | 2.0 | 0.2 |
| 90 min. | 1.1 | 1.2 | 1.3 | 2.9 |
| CA Coastal | | | | |
| Original Pyrolyzed | 1.3 | 2.6 | 3.4 | <0.01 |
| 60 min. | 1.0 | b | — | 4.4 |
| 90 min. | 1.1 | b | — | 7.9 |
| Boscan | | | | |
| Original Pyrolyzed | 1.7 | 3.2 | 5.4 | <0.01 |
| 60 min. | 1.1 | 1.3 | 1.4 | 7.5 |
| 90 min. | 1.0 | 1.4 | 1.4 | 11.2 |
| MaxCL | | | | |
| Original Pyrolyzed | 1.8 | 3.1 | 5.6 | <0.01 |
| 90 min | 1.0 | 1.2 | 1.2 | 7.0 |
| Vistar | | | | |
| Original Pyrolyzed | 1.6 | 2.6 | 4.2 | <0.01 |
| 60 min. | 1.2 | 1.6 | 1.9 | 0.2 |
| 90 min. | 1.0 | b | — | 6.2 |

[a]Weight percent of toluene soluble material
[b]Heithaus titration not possible due to multi phase product It becomes apparent upon review of the plotted data, that a hydrocarbon material may have sufficient association between components to manifest unimodal characteristics such as a size ratio of the core material and the solvated core material ($K_s$) when $K_s$ has a value equal to or greater than about 1.1, or a size ratio of a plurality of solvated core materials (with associated solvent) solvated core materials ($K_F$) when $K_F$ has a value equal to or greater than about 1.4, or a sufficient solvation shell (K) when K has a value equal to or greater than about 1.5. For example, hydrocarbon materials having unimodal characteristics may comprise an amount of asphaltenes having polarity, an amount of solvents having lower polarity than the asphaltenes, and a sufficient amount of resins having a polarity intermediate to the polarity of the asphaltenes and the lower polarity of the solvents to establish a salvation shell $(K)=(K_{s \cdot KF})$ at a value equal to or greater than about 1.5. These ascertainable measures of the unimodal characteristics of hydrocarbons with respect to $K_S$ $K_F$ and K constitute important embodiments of the invention.

As can easily understood, $K_S$, $K_F$, and K for a particular hydrocarbon material may be as indicia of stability for the unimodal characteristics of a hydrocarbon material. A first indicia of stability may comprise determining an average size ratio of the solvated core material to the core material itself (indicia of stability$_{Ks}$), or determining an average size ratio of associated solvent around a plurality of solvated core materials to the solvated core material itself (indicia of stability$_{KF}$), or determining a size ratio of the associated solvent and solvation shell to the core material itself (indicia of stability$_K$). Naturally, these relationships could be expressed in other terms or by the use of other devices and still provide effective indicia of stability.

Naturally, these size ratios may be determined using a variety of instruments such as a nuclear magnetic resonance spectroscopy device, a nuclear magnetic resonance tomography device, a mass spectrometry device, an infrared spectrometry device, a microscope device, a raman spectroscopy device, a size exclusion chromatography device, a gel electrophoresis device, or a paper chromatography device. The size ratios may be determined prior to processing of the hydrocarbon material or during processing of the hydrocarbon material. For example, nuclear magnetic resonance imaging has shown that at least two distinct phases are present after pyrolysis with subsequent coke formation.

It can be further understood that establishing a threshold of instability for unimodal characteristics of hydrocarbon materials may comprise assigning a threshold of instability to size ratios having a value of $K_S$ at about 1.1, or $K_F$ at about 1.4, or K at about 1.5. Below these values the level of association between components in a hydrocarbon material may be insufficient to exhibit unimodal character and transition to multimodal character may be initiated including heterogenous mixture formation, carbon deposition, or coke formation. Importantly, various embodiments of the invention allow for comparison of determined indicia of stability to the determined thresholds of instability with respect to $K_S$, $K_F$, or K so that the proximity of a particular hydrocarbon material to formation of multimodal characteristics. This may comprise comparing the value of $K_S$ for a given hydrocarbon material to the threshold of instability value of $K_S$. Similarly, the value of $K_F$ for a given hydrocarbon material to the threshold of instability value of $K_F$, or the value of K for a given hydrocarbon material to the threshold of instability value of K. An approach which was not used prior to the instant invention.

Another embodiment of the invention can be based upon the free solvent volume of the hydrocarbon material. The free solvent volume of hydrocarbon materials having unimodal character relates to the fraction of the total solvent that is not associated with the core materials or associated with or trapped by a plurality of solvated core materials. This indicia of stability can correlate with the amount of initial carbonaceous deposition, including coke formation, below pyrolysis temperatures or the initial amount of carbonaceous deposition formed in the early stages of a pyrolytic process. This indicia of stability does not include the amount of carbonaceous deposition when pyrolysis is carried to completion. The total amount of carbonaceous deposition, including deposition of coke, may be estimated by further determining the hydrogen-carbon ratio of the hydrocarbon material. This ratio is subsequently used to calculate the weight of the total carbon content of an amount of hydrocarbon material as would be well known to those with skill in the art. With respect to free solvent volume ($\Phi_{FS}$), one manner of determining $\Phi_{FS}$ comprises $\Phi_{FS}=[1-K_s\,(1/1-p_a)(\chi_a/1.2)]$. The average $K_s$ for unpyrolyzed hydrocarbon material value can be about 1.6. Values for $\Phi_{FS}$ correlate to deposition of carbonaceous material when the value for $K_s$ is held constant Thus the only measurements which may be required to determine $\Phi_{FS}=[1-K_s\,(1/1-p_a)(\chi_a/1.2))]$ in this manner can be the value of weight percent heptane asphaltenes ($X_a$ and the value of petizabiltiy of asphaltenes ($p_a$). Other methods of determining free solvent volume, or modifying the values relating structure consideration such as H/C ratio, or fraction of bridge head aromatic carbons may be used, and are encompassed by the invention.

Regarding this embodiment of the invention, the weight percent heptane asphaltenes ($\chi_a$) and the value of petizabiltiy of asphaltenes ($p_a$) may be determined as discussed above. Keeping in mind that the concept can work with other precipitating solvents and other dissolvents as discussed.

The $p_a$ $\chi_a$ and the $\phi_{FS}$ for five hydrocarbon materials having unimodal characteristics were determined The data for these determinations was compiled and provided in Table 10.

TABLE 10

Free Solvent Volumes at 25° C.

| Residuum | $\chi/1.2$ | $\rho_a$ | $\phi_{ps}$[a] |
|---|---|---|---|
| Redwater, B.C. | 0.097 | 0.698 | 0.49 |
| CA Coastal | 0.164 | .0614 | 0.32 |
| Boscan | 0.165 | 0.691 | 0.14 |
| MaxCL | 0.151 | 0.682 | 0.24 |
| Vistar | 0.150 | 0.616 | 0.38 |

[a]$K_S$ = 1.6

The five hydrocarbon materials were pyrolyzed in five (5) gram reactor tubes at 400° C. for 90 minutes. The initial amount of carbonaceous deposition, including coke deposition, is set out for each hydrocarbon material in Table 11.

TABLE 11

Initial Coke Make in Tube Reactor for 90 Minutes at 400° C.

| Residuum | Toluene Insolubles (Coke), Wt. % |
|---|---|
| Redwater, B.C. | 1.3 |
| CA Coastal | 7.2 |
| Boscan | 10.6 |
| MaxCL | 8.4 |
| Vistar | 4.3 |

Figure 13:
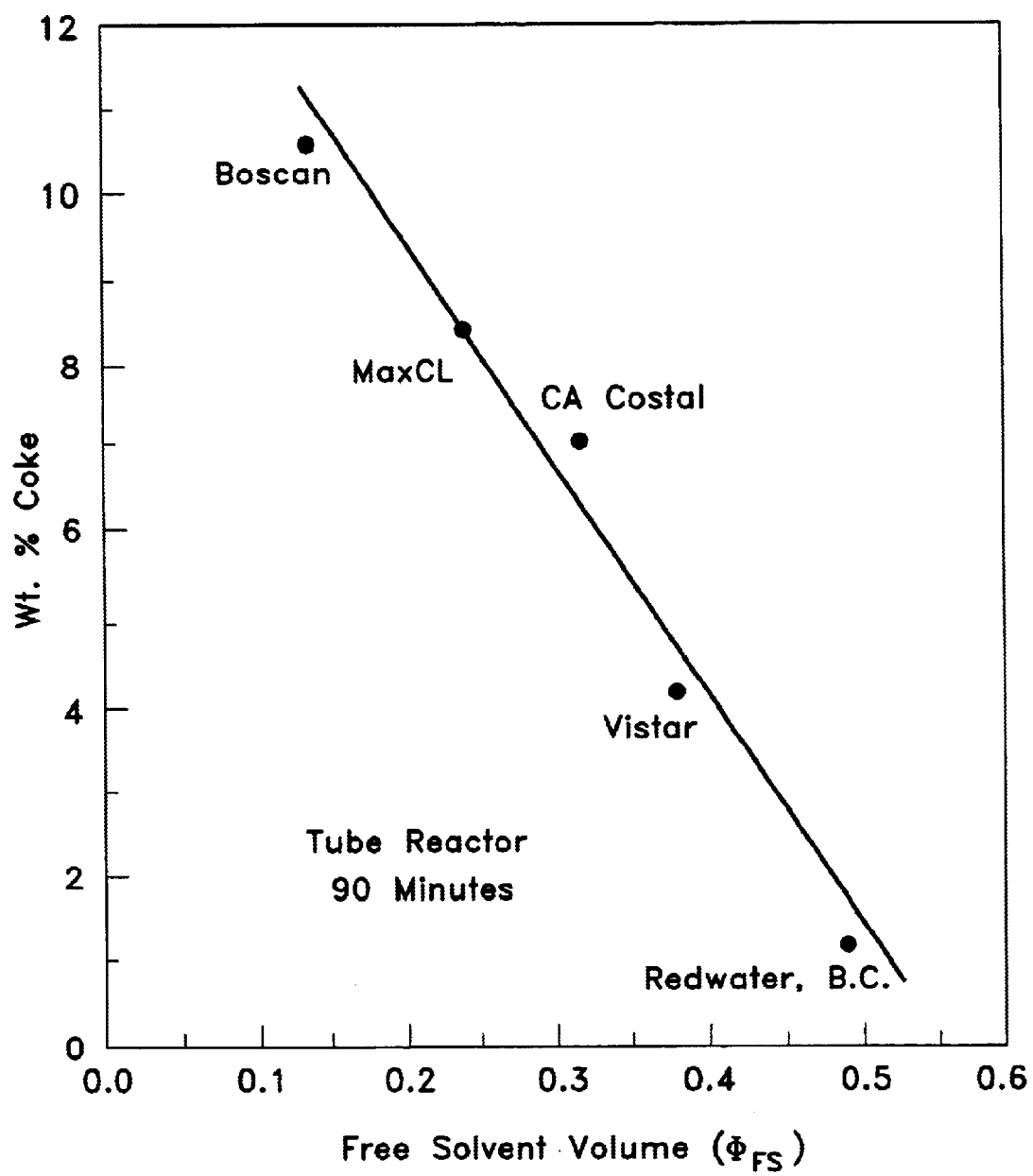
FIG. 13 shows a graph of weight percent coke relative to values for the indica of stability$_{\phi FS}$.

Now referring to FIG. 13, which is a plot of initial deposition of carbonaceous material versus $\Phi_{FS}$. As can be understood, from the plot as $\Phi_{FS}$ decreases the amount of initial carbonaceous material that forms increases for a given set of processing parameters. As such, an embodiment of the invention provides an indica of stability based upon $\Phi_{FS}$ with respect to predicting the amount of initial carbonaceous deposition Moreover, plots of initial carbonaceous material formation versus $\Phi_{FS}$ could be generated for any variety of hydrocarbon materials for particular processing conditions, such as different pyrolysis temperatures or for different pyrolysis times or in various combinations, to rank the hydrocarbon materials in terms of relative carbon deposition potential based upon $\Phi_{FS}$.

As can be further understood additional embodiments of the invention may include selecting distillation parameters to distill hydrocarbon material having unimodal characteristics use predetermined indicia of stability to avoid reaching the threshold of instability. By distilling hydrocarbon material using distillation parameters that take into account or compare the indica of stability to the threshold of stability, prior to or during the distillation process or other processing event, it may be possible to select distillation parameters to allow substantially continuous distillation avoiding the threshold of instability for said unimodal characteristics. Specifically, selecting distillation parameters having predetermined indicia of stability may avoid or limit coke formation. Importantly, a method of processing hydrocarbon material using distillation parameters based upon indicia of stability, indicia of instability, independently or in cooperation, may allow distillation of hydrocarbon materials so as to have ascertainable indicia of stability in closer proximity to the threshold of instability compared to typical distillation parameters. By processing a hydrocarbon material so that the indicia of stability are closer to the threshold of instability in a substantially continuous distillation event, the output of liquid distillables per unit amount of said hydrocarbon material may be increased by comparison with typical parameters of distillation. As described above, an increase in the amount of liquid distillables from the same amount of hydrocarbon material may decrease the amount of energy used per unit of liquid distillate produced, or may also reduce the amount of emissions generated per unit of liquid distillate produced Such reduction in emissions may be a reduction in carbon dioxide. Moreover, when hydrocarbon materials are distilled in a continuous distillation event it may increase the purity of at least a portion of said liquid distillates.

Another embodiment of the invention, understandably includes, the selection of hydrocarbon materials for purchase or processing based upon determined indica of stability for the degree of unimodal characteristics. Naturally, some hydrocarbon materials which have indicia of stability which show a high level of unimodal characteristics may have greater desirability for some parameters of processing. Alternately, with respect to some embodiments of the invention selecting distillation parameters for hydrocarbon material having unimodal characteristics may designed to reach a predetermined level of instability characteristics. As such, distilling these hydrocarbon materials using such distillation parameters may continue until reaching said predetermined level of instability characteristics. A method of processing hydrocarbon material in this fashion initiate the formation of a predetermined amount of carbon or coke. Again as above, such distillation parameters may allow for maintaining continuous distillation until reaching the predetermined level of instability characteristics.

Naturally, because products from these processes may be distinguished from conventional processing by their purity an embodiment of the invention comprises the isolation of these higher purity products.

As mentioned earlier, this invention can be embodied in a variety of ways. In addition, each of the various elements of the invention and claims may also be achieved in a variety of manners. This disclosure should be understood to encompass each such variation, be it a variation of an embodiment of any apparatus embodiment, a method or process embodiment, or even merely a variation of any element of these. Particularly, it should be understood that as the disclosure relates to elements of the invention, the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled. As but one example, it should be understood that all action may be expressed as a means for taking that action or as an element which causes that action. Similarly, each physical element disclosed should be understood to encompass a disclosure of the action which that physical element facilitates. Regarding this last aspect, as but one example, the disclosure of a "dissolvent" should be understood to encompass disclosure of the act of "dissolving"—whether explicitly discussed or not—and, conversely, were there only disclosure of the act of "dissolving", such a disclosure should be understood to encompass disclosure of a "dissolvent." Such changes and alternative terms are to be understood to be explicitly included in the description.

The foregoing discussion and the claims which follow describe the preferred embodiments of the invention. Particularly with respect to the claims it should be understood that changes may be made without departing from their essence. In this regard it is intended that such changes would still fall within the scope of the present invention. It is simply not practical to describe and claim all possible revisions which may be accomplished to the present invention. To the extent such revisions utilize the essence of the invention each would naturally fall within the breadth of protection accomplished by this patent. This is particularly true for the present invention since its basic concepts and understandings are fundamental in nature and can be applied in a variety of ways to a variety of fields.

Any references mentioned, including but not limited to federal or state statutes, patents, publications, brochures, marketing materials, or inter-net pages, in this patent application, are hereby incorporated by reference or should be considered as additional text or as an additional exhibits or attachments to this application to the extent permitted; however, to the extent statements might be considered inconsistent with the patenting of this/these invention(s) such statements are expressly not to be considered as made by the applicant. Further, the disclosure should be understood to include support for each feature, component, and step shown as separate and independent inventions as well as the various combinations and permutations of each.

In addition, unless the context requires otherwise, it should be understood that the term "comprise" or variations such as "comprises" or "comprising", are intended to imply the inclusion of a stated element or step or group of elements or steps but not the exclusion of any other element or step or group of elements or steps. Such terms should be interpreted in their most expansive form so as to afford the applicant the broadest coverage legally permissible in countries such as Australia and the like. Such terms are intended to have an inclusive meaning rather than an exclusive one and should be interpreted in their most expansive form so as to afford the applicant the broadest coverage legally permissible. Therefore, in countries such as Australia and the like, such terms are not intended to have an exclusive, or more limited meaning. Thus, the applicant should be understood to claim at least: i) a molecular weight/polarity map system; ii) each of the coking indexes; iii) a system of pre-distillation evaluation of hydrocarbon material; iv) a nearly continuous distillation system; v) a system for optimizing the yields of distillable liquids; vi) a system for determining the coking indexes; vii) the resulting products; viii) the related methods disclosed and described, ix) similar, equivalent, and even implicit variations of each of these devices and methods; x) those alternative designs which accomplish each of the functions shown as are disclosed and described; xi) those alternative designs and methods which accomplish each of the functions shown as are implicit to accomplish that which is disclosed and described; xii) each feature, component, device, and step shown as separate and independent inventions; xiii) the combinations of applied systems including the designs disclosed, xiv) the resulting products produced by such systems or components, xv) related methods including the techniques of the applied systems, and xvi) the various combinations and permutations of each of the above.

We claim:

1. A method of processing petroleum residua, comprising the steps of:
   a. providing an amount of said petroleum residua having solvated asphaltenes dispersed in said petroleum residua;
   b. precipitating an amount of said asphaltenes from said amount of said petroleum residua with a first solvent and determining said amount of precipitated asphaltenes;
   c. dissolving at least part of said amount of said precipitated asphaltenes in a second solvent with a polarity between a polarity of said first solvent and a polarity of a third solvent capable of dissolving said amount of said asphaltenes completely;
   d. determining a proximity to a threshold of instability value of said petroleum residua, wherein said threshold of instability value relates to an amount of said asphaltenes dissolved in said second solvent; and
   e. processing said petroleum residua under conditions that maintain a value for said petroleum residua that avoids said threshold of instability value.

2. A method of processing petroleum residua as described in claim 1, wherein said step (d) of determining a proximity to a threshold of instability value of said petroleum residua comprises utilizing a value of $K_S$ for said petroleum residua, wherein $K_S$ is a ratio of a solvated core material size to a core material size for solvated asphaltenes, thus representing an amount of solvent adsorbed around said core material, and wherein said step (e) of processing said petroleum residua comprises processing said petroleum residua under conditions that maintain $K_S$ equal to or greater than about 1 1.

3. The method of processing petroleum residua as described in claim 1, wherein said step (a) of providing an amount of said petroleum residua having solvated asphaltenes dispersed in said petroleum residua comprises selecting said petroleum residua from the group consisting of coal tars, shale oils, tar sand bitumen, asphalts, and heavy oils.

4. The method of processing petroleum residua as described in claim 2, wherein $K_S=(1/(1-\chi_{cy}))$, wherein $\chi_{cy}$ is a weight fraction of heptane asphaltenes soluble in cyclohexane.

5. The method of processing petroleum residua as described in claim 1, wherein said step (b) of precipitating an amount of said asphaltenes from said amount of said petroleum residua with a first solvent comprises selecting said first solvent from the group consisting of iso-octane, pentane, hexane, and heptane.

6. The method of processing petroleum residua as described in claim 1, wherein said step (c) of dissolving at least part of said amount of said precipitated asphaltenes in a second solvent comprises selecting said second solvent from the group consisting of cyclohexane, pentane, hexane, heptane, and heptane:toluene (1:1)(v:v).

7. A method of processing petroleum residua as described in claim 1 wherein said step (d) of determining a proximity to a threshold of instability value of said petroleum residua comprises utilizing a value for a ratio of an amount of said asphaltenes dissolved in said second solvent to said amount of precipitated asphaltenes.

8. A liquid distillate produced in accordance with the method of claim 1.

9. A method of analyzing petroleum residua comprising the steps of:
   a. mixing an amount of said petroleum residua $W_a$ into an amount of aromatic solvent $V_s$;

b. titrating aromatic solvent soluble components in said amount of aromatic solvent $V_s$ with an amount of weak aliphatic solvent $V_t$ until a flocculation occurs;

c. calculating a flocculation ratio at infinite dilution $FR_{max}$ from an equation $FR_{max}=V_s/(V_s+V_t)$;

d. calculating a dilution concentration at zero aromatic solvent level $C_{min}$ from an equation $C_{min}=W_a/(V_s+V_t)$ wherein $V_s=0$;

e. determining a peptizability of asphaltenes $p_a$ from an equation $p_a=1-FR_{max}$; and f determining a value of $p_a/C_{min}$.

10. The method of analyzing petroleum residua as described in claim 9, wherein said step (a) of mixing an amount of said petroleum residua $W_a$ into an amount of aromatic solvent $V_s$ comprises mixing an amount of said petroleum residua into an amount of toluene.

11. The method of analyzing petroleum residua as described in claim 9, wherein said step (b) of titrating aromatic solvent soluble components in said amount of aromatic solvent $V_s$ with an amount of weak aliphatic solvent $V_t$ until a flocculation occurs comprises titrating aromatic solvent soluble components in an amount of aromatic solvent $V_s$ with an amount of iso-octane until a flocculation occurs.

12. The method of analyzing petroleum residua as described in claim 9, further comprising the step of comparing said value of $p_a/C_{min}$ for toluene soluble components with a threshold of instability $p_a/C_{min}$ being within the range of about 0.1 to about 0.4.

13. A method of processing petroleum residua comprising the steps of a. providing an amount of said petroleum residua $W_a$ having solvated asphaltenes dispersed in said petroleum residua;

a. mixing said amount of said petroleum residua $W_a$ into an amount of aromatic solvent $V_s$;

b. titrating aromatic solvent soluble components in said amount of aromatic solvent $V_s$ with an amount of weak aliphatic solvent $V_t$ until a flocculation occurs, d. determining a proximity to a threshold of instability value of said petroleum residua, as a result of said steps (a) of providing an amount of said petroleum residua $W_a$ having solvated asphaltenes dispersed in said petroleum residua and (b) of mixing said amount of said petroleum residua $W_a$ into an amount of aromatic solvent $V_s$, utilizing a value of $K_F$, wherein $K_F$ is a ratio of an average size of a plurality of solvated core materials with an associated solvent to an average size of a plurality of solvated core materials, thus representing an amount of said associated solvent associated with said plurality of solvated core materials; and e. processing said petroleum residua under conditions that maintain $K_F$ equal to or greater than about 1.4.

14. The method as described in claim 1 or 13, further comprising processing said petroleum residua under conditions that maintain a solvation shell value of K equal to or greater than about 1.5, wherein $K=K_S \cdot K_F$, wherein $K_S$ is a ratio of a solvated core material size to a core material size for solvated asphaltenes, thus representing an amount of solvent adsorbed around said core material, and $K_F$ is a ratio of an average size of a plurality of solvated core materials with an associated solvent to an average size of a plurality of solvated core materials, thus representing an amount of said associated solvent associated with said plurality of solvated core materials.

15. The method of processing petroleum residua as described in claim 13, wherein $K_F=(1/(1-p_a))$, wherein $p_a$ is a value of peptizability of asphaltenes.

16. A liquid distillate produced in accordance with the method of claim 13.

17. The method as described in claim 1, 9 or 13, further comprising the step of predicting a proximity of said petroleum residua to coke formation.

18. The method as described in claim 1, 9 or 13, further comprising the steps of:

a. selecting distillation parameters of said petroleum residua to avoid reaching a threshold of instability;

b. distilling said petroleum residua using said distillation parameters; and c. avoiding said threshold of instability.

19. The method as described in claim 18, wherein said step (a) of selecting distillation parameters of said petroleum residua to avoid reaching said threshold of instability comprises selecting distillation parameters to avoid coke formation.

20. The method as described in claim 18, further comprising the step of maintaining continuous distillation of said petroleum residua.

21. The method as described in claim 18, wherein said step (b) of distilling said petroleum residua using said distillation parameters comprises distilling said petroleum residua to closer proximity of said threshold of instability compared to typical distillation parameters.

22. The method as described in claim 1, 9 or 13, further comprising the steps of:

a selecting distillation parameters for said petroleum residua to reach a predetermined level of stability;

b. distilling said petroleum residua using said distillation parameters; and c. continuing distillation of said petroleum residua until reaching said predetermined level of stability.

23. The method as described in claim 22, wherein said step (c) of reaching said predetermined level of stability comprises initiating formation of a predetermined amount of coke.

24. The method as described in claim 22, further comprising the step of maintaining continuous distillation until reaching said predetermined level of stability.

25. The method as described in claim 22, further comprising the step of determining a hydrogen-carbon ratio of said petroleum residua.

26. The method as described in claim 22, further comprising the step of determining a total amount of coke, which may form from said petroleum residua.

27. The method as described in claim 22, further comprising the step of increasing output of liquid distillate per unit amount of said petroleum residua.

28. The method as described in claim 22, further comprising the step of decreasing an amount of energy used per unit of liquid distillate produced.

29. The method as described in claim 22, further comprising the step of reducing an amount of emissions generated per unit of liquid distillate produced.

30. The method as described in claim 29, wherein said step of reducing said amount of emissions generated per unit of liquid distillate produced comprises reducing carbon dioxide emissions.

31. The method as described in claim 22, further comprising the step of increasing a purity of at least a portion of liquid distillates produced.

32. A liquid distillate produced in accordance with the method of claim 9.

* * * * *

UNITED STATES PATENT AND TRADEMARK OFFICE
CERTIFICATE OF CORRECTION

| | | |
|---|---|---|
| PATENT NO. | : 6,773,921 B1 | Page 1 of 1 |
| APPLICATION NO. | : 10/009863 | |
| DATED | : August 10, 2004 | |
| INVENTOR(S) | : John F. Schabron and Joseph F. Rovani, Jr. | |

It is certified that error appears in the above-identified patent and that said Letters Patent is hereby corrected as shown below:

*The following paragraph should appear at Column 1, line 10:*

ACKNOWLEDGMENT OF GOVERNMENT SUPPORT

This patent relates to work performed under U.S. DOE Cooperative Agreement #DE-FC26-98FT40322. The U.S. government may have certain rights in this inventive technology, including "march-in" rights, as provided for by the terms of U.S. DOE Cooperative Agreement #DE-FC26-98FT40322.

Signed and Sealed this

Sixth Day of July, 2010

David J. Kappos
*Director of the United States Patent and Trademark Office*